(12) United States Patent
Beaty

(10) Patent No.: US 10,337,046 B2
(45) Date of Patent: Jul. 2, 2019

(54) HIGH CONFIDENCE IN POSITIVE STATUS DETERMINATION

(75) Inventor: Patrick Shawn Beaty, Dallastown, PA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 1293 days.

(21) Appl. No.: 12/918,019

(22) PCT Filed: Feb. 19, 2008

(86) PCT No.: PCT/US2008/002175
§ 371 (c)(1),
(2), (4) Date: Oct. 19, 2010

(87) PCT Pub. No.: WO2009/105063
PCT Pub. Date: Aug. 27, 2009

(65) Prior Publication Data
US 2011/0029252 A1    Feb. 3, 2011

(51) Int. Cl.
C12Q 1/04          (2006.01)
(52) U.S. Cl.
CPC ..................... C12Q 1/04 (2013.01)
(58) Field of Classification Search
CPC ....................................................... C12Q 1/04
USPC ......................................................... 702/19
See application file for complete search history.

(56) References Cited

U.S. PATENT DOCUMENTS

| | | | |
|---|---|---|---|
| 4,889,992 A | 12/1989 | Hoberman | |
| 5,637,501 A | 6/1997 | Ollar et al. | |
| 5,814,474 A | 9/1998 | Berndt | |
| 6,074,870 A * | 6/2000 | Berndt | 435/287.5 |
| 6,096,272 A | 8/2000 | Clark et al. | |
| 6,432,697 B1 | 8/2002 | Tice et al. | |
| 6,617,127 B2 | 9/2003 | Quaedflieg et al. | |
| 6,900,030 B2 | 5/2005 | Pitner et al. | |
| 6,925,389 B2 * | 8/2005 | Hitt et al. | 702/19 |
| 6,950,752 B1 * | 9/2005 | Friend et al. | 702/19 |
| 6,991,918 B2 * | 1/2006 | Keith | 435/31 |
| 7,057,721 B2 * | 6/2006 | Gardner et al. | 356/301 |
| 2002/0155424 A1 | 10/2002 | Pitner et al. | |
| 2003/0097059 A1 * | 5/2003 | Sorrell et al. | 600/420 |
| 2005/0069863 A1 * | 3/2005 | Moraleda et al. | 435/4 |
| 2006/0115824 A1 | 6/2006 | Samadpour | |
| 2006/0190192 A1 * | 8/2006 | Willey et al. | 702/20 |
| 2007/0032706 A1 * | 2/2007 | Kamath et al. | 600/300 |

FOREIGN PATENT DOCUMENTS

| | | |
|---|---|---|
| EP | 0697460 B1 | 11/2001 |
| JP | 08-062138 | 3/1996 |
| JP | 2002-501363 | 1/2002 |
| WO | 9812348 A1 | 3/1998 |
| WO | 2005103284 A2 | 11/2005 |

OTHER PUBLICATIONS

International Search Report and Written Opinion for Application No. PC/US08/02175 dated Jul. 23, 2008.
Oberoi et al., "Comparison of rapid colorimetric method with conventional method in the isolation of *Mycobacterium tuberculosis*," Indian J Med Microbial 22:44-46, 2004.
Stanier et al., 1986, The Microbial World, 5th edition, Prentice-Hall, Englewood Cliffs, New Jersey, pp. 10-20, 33-37, and 190-195.
Extended European Search Report for Application No. 08725773.9 dated Dec. 27, 2011.
Extended European Search Report for Application No. EP08779567 dated Dec. 27, 2011.
Extended European Search Report for Application No. EP15161700.8 dated Jun. 30, 2015.
International Search Report and Written Opinion for Application No. PCT/US08/02175 dated Jul. 23, 2008.
Becton, Dickinson and Company "Automated Blood Culture BACTEC™, 9240/9120/9050", Revision B, pp. 1-21, https://legacy.bd.com/ds/technicalCenter/clsi/clsi-9000bc2.pdf, Jul. 25, 2001 (Jul. 25, 2001).
Canadian Office Action received in 2,715,569 dated Aug. 1, 2018, pp. 6.

* cited by examiner

*Primary Examiner* — Jerry Lin
(74) *Attorney, Agent, or Firm* — Botos Churchill IP Law LLP

(57) ABSTRACT

Systems, methods, and apparatus for determining whether a culture in a vessel contains a plurality of microorganisms are provided. A normalization relative value is calculated for each respective measurement of a biological state of the culture between (i) the respective measurement and (ii) an initial biological state. For each fixed interval of time points, a derivative of the normalization relative values in the interval of time points is calculated, thereby forming a plurality of rate transformation values. For each set of rate transformation values in the plurality of rate transformation values, a measure of central tendency of the values in the set is computed, thereby forming a plurality of average relative transformation values. A determination whether the culture contains the microorganisms is made based on whether any calculated average relative transformation value exceeds a first threshold or whether an extent of growth exhibited by the culture exceeds a second threshold.

20 Claims, 10 Drawing Sheets

HIGH CONFIDENCE IN POSITIVE STATUS DETERMINATION

CROSS-REFERENCE TO RELATED APPLICATIONS

The present application is a national phase entry under 35 U.S.C. § 371 of International Application No. PCT/US2008/002175, which was filed on Feb. 19, 2008 and published in English as International Publication No. WO 2009/105063 A1.

1 FIELD OF THE INVENTION

Disclosed are improved systems and methods for determining that a culture in a vessel contains microorganisms.

2 BACKGROUND OF THE INVENTION

Rapid and reliable detection of microorganisms in a culture, such as a blood culture, is among the most important functions of the clinical microbiology laboratory. Currently, the presence of biologically active agents such as bacteria in a patient's body fluid, and especially in blood, is determined using culture vials. A small quantity of the patient's body fluid is injected through an enclosing rubber septum into a sterile vial containing a culture medium and the vial is then incubated and monitored for microorganism growth.

Common visual inspection of the culture vial then involves monitoring the turbidity or observing eventual color changes of the liquid suspension within the vial. Known instrument methods can also be used to detect changes in the carbon dioxide content of the culture vessels, which is a metabolic byproduct of the bacterial growth. Monitoring the carbon dioxide content can be accomplished by methods well established in the art.

In some instances, non-invasive infrared microorganism detection instrument is used in which special vials having infrared-transmitting windows are utilized. In some instances, glass vials are transferred to an infrared spectrometer by an automated manipulator arm and measured through the glass vial. In some instances, chemical sensors are disposed inside the vial. These sensors respond to changes in the carbon dioxide concentration in the liquid phase by changing their color or by changing their fluorescence intensity. These techniques are based on light intensity measurements and require spectral filtering in the excitation and/or emission signals.

As the above indicates, several different culture systems and approaches are available to laboratories. For example, the BACTEC® radiometric and nonradiometric systems (Becton Dickenson Diagnostic Instrument Systems, Sparks, Md.) are often used for this task. The BACTEC® 9240 instrument, for example, accommodates up to 240 culture vessels and serves as an incubator, agitator, and detection system. Each vessel contains a fluorescent $CO_2$ sensor, and the sensors are monitored on a continuous basis (e.g., every ten minutes). Cultures are recognized as positive by computer algorithms for growth detection based on an increasing rate of change as well as sustained increase in $CO_2$ production rather than by the use of growth index threshold or delta values. The BACTEC® 9240 is completely automated once the vessels have been loaded.

One drawback with these microorganism detection approaches is that they do not always detect cultures that contain microorganisms. Thus, what are needed in each of the above-identified systems are improved methods for determining whether a culture in a vessel contains a plurality of microorganisms.

3 SUMMARY OF THE INVENTION

To meet the needs identified in the prior art, the present invention, in one aspect, provides systems, methods and apparatus that allow an increased confidence level in the notification of vessel positive status in culture systems. The present invention advantageously provides a high confidence positive status in a blood culture.

The present invention utilizes the difference in rate of metabolic change and extent of change to provide information about the confidence in a positive status change on an individual vessel basis. the present invention describes a data transformation that can be applied to metabolic or cell growth data in a way that provides confidence that a culture in a vessel is infected with a microorganism (high confidence positive) and essentially eliminates the potential for false negative determinations as they currently exist in known culture systems. The high confidence positive can, for example, be applied to cases when growth has begun but the vial was not being measured. An example is the case when a vessel encounters significant delays between the time the specimen was collected into the vessel and the time the vessel enters the measuring instrument. The high confidence positive algorithm can be applied to vessels that have measurement reading gaps resulting from a number of causes including loss of power, instrument failure and down time due to service. The user benefit is a decreased requirement to subculture vessels that have encountered these types of protocol interruptions. Further, the high confidence positive may be linked to positive test procedures as a biological quantification metric. For example, a culture may be detected as positive at an average rate change value (ART) value of 100, the cell mass of an ART=200 may be required to perform a rapid identification or molecular characterization of the microorganism present, and an ART value >400 may require dilution prior to rapid identification or gene typing procedures.

In one aspect, the present invention provides a method of determining whether a culture in a vessel contains a plurality of microorganisms. In the method a normalization relative value is calculated for each respective measurement in a plurality of measurements of a biological state of the culture in the vessel, taken at different time points between a first time point and a second time point, between (i) the respective measurement and (ii) an initial biological state of the culture taken at an initial time point, thereby forming a plurality of normalization relative values.

The plurality of normalization relative values can be broken down, on a timewise basis, into predetermined fixed intervals of time points between the first time point and the second time point. For instance, a first predetermined fixed interval may include the first ten normalization relative values, a second predetermined fixed interval may include the next ten normalization relative values, and so forth until the second time point is reached. For each of these respective predetermined fixed intervals of time points between the first time point and the second time point, a first derivative of the normalization relative values in the respective predetermined fixed interval is determined, thereby forming a plurality of rate transformation values.

There is a rate transformation value for each predetermined fixed interval of time points. The plurality of rate transformation values can be considered as comprising a plurality of sets of rate transformation values. Each respective set of rate transformation values is for a different set of contiguous time points between the first time point and the second time point. For example, the first set of rate transformation values may be the first seven rate transformation values in the plurality of rate transformation values, the second set of rate transformation values may be the next seven rate transformation values in the plurality of rate transformation values, and so forth. For each respective set of rate transformation values in the plurality of sets of rate transformation values, an average relative transformation value is computed as a measure of central tendency of each of the rate transformation values in the respective set of rate transformation values. In this way, a plurality of average relative transformation values is computed.

Further, in the method, either (i) a first result, (ii) a second result, or (iii) both a first or second result is obtained. The first result is based on a determination of whether any average relative transformation value in the plurality of average relative transformation values exceeds a first threshold value. The second result is based on a determination of whether an extent of growth exhibited by the culture exceeds a second threshold value. The first result or the second result is used to determine whether the culture in the vessel contains the plurality of microorganisms.

In some embodiments, the method further comprises outputting the first result, the second result, or a determination of whether the culture in the vessel contains the plurality of microorganisms to a user interface device, a monitor, a computer-readable storage medium, a computer-readable memory, or a local or remote computer system. In some embodiments, the first result, the second result, or the determination of whether the culture in the vessel contains the plurality of microorganisms is displayed.

In some embodiments, the first time point is five or more minutes after the initial time point and the final time point is thirty or more hours after the initial time point. In some embodiments, the first time point is between 0.5 hours and 3 hours after the initial time point and the final time point is between 4.5 hours and twenty hours after the initial time point. In some embodiments, the measure of central tendency of the rate transformation values in a first set of rate transformation values in the plurality of sets of rate transformation values comprises (i) a geometric mean, an arithmetic mean, a median, or a mode of each of the rate transformation values in the first set of rate transformation values.

In some embodiments, the measurements in the plurality of measurements of the biological state of the culture are each taken of the culture at a periodic time interval between the first time point and the second time point. In some embodiments, the periodic time interval is an amount of time between one minute and twenty minutes, between five minutes and fifteen minutes, or between 0.5 minutes and 120 minutes.

In some embodiments, the initial biological state of the culture is determined by a fluorescence output of a sensor that is in contact with the culture. For instance, in some embodiments, the amount of fluorescence output of the sensor is affected by $CO_2$ concentration, $O_2$ concentration, or pH.

In some embodiments, between 10 and 50,000 measurements, between 100 and 10,000 measurements, or between 150 and 5,000 measurements of the biological state of the culture in the vessel are in the plurality of measurements of the biological state of the culture. In some embodiments, each respective predetermined fixed interval of time points comprises or consists of each of the rate transformation values for time points in a time window between the first time point and the second time point, where the time window is a period of time that is between twenty minutes and ten hours, twenty minutes and two hours, or thirty minutes and ninety minutes.

In some embodiments, each set of rate transformation values in the plurality of rate transformation values comprises or consists of between four and twenty, between five and fifteen, or between 2 and 100 contiguous rate transformation values. In some embodiments, there are between five and five hundred or between twenty and one hundred average relative transformation values in the plurality of average relative transformation values. In some embodiments, a volume of the culture is between 1 ml and 40 ml, between 2 ml and 10 ml, less than 100 ml, or greater than 100 ml.

In some embodiments, the vessel contains a sensor composition in fluid communication with the culture, where the sensor composition comprises a luminescent compound that exhibits a change in luminescent property, when irradiated with light containing wavelengths that cause said luminescent compound to luminesce, upon exposure to oxygen, and where the presence of the sensor composition is non-destructive to the culture and where the initial biological state of the culture is measured by the method of (i) irradiating the sensor composition with light containing wavelengths that cause the luminescent compound to luminesce and (ii) observing the luminescent light intensity from the luminescent compound while irradiating the sensor composition with the light. In some embodiments, the luminescent compound is contained within a matrix that is relatively impermeable to water and non-gaseous solutes, but which has a high permeability to oxygen. In some embodiments, the matrix comprises rubber or plastic.

In some embodiments, the extent of growth (EG) is the maximum normalization relative value in the plurality of normalization relative values. In some embodiments, the extent of growth is determined by the equation:

$$EG = NR_{after\_growth} - NR_{minimum\_growth}$$

where $NR_{after\_growth}$ is a normalization relative value in the plurality of normalization relative values that was used in the calculation of (i) the first average relative transformation value following a maximum average relative transformation value, (ii) a maximum average relative transformation value, or (iii) a first average relative transformation value preceding the maximum average relative transformation value in the plurality of average relative transformation values, and $NR_{minimum\_growth}$ is a normalization relative value in the plurality of normalization relative values that was used in the calculation of the first average relative transformation value to achieve a third threshold value. In some embodiments, the third threshold value is a value between 5 and 100 or a value between 25 and 75.

Advantageously, using the novel systems, methods, and apparatus of the present invention, an incubating system, such as the BACTEC® blood culture system, can be programmed to determine whether a culture is infected with microorganisms before manual tests, such as a Gram stain or a subculture, are performed. Briefly, a culture is identified as positive for microorganism infection by an incubator by analyzing novel parameters (e.g., average relative transformation value, extent of growth exhibited by the culture) associated with microorganism metabolism. Such cultures will have increased metabolism relative to uninfected cultures and, on this basis, microorganism infection can be detected. While the tests disclosed herein are most accurate when a single microorganism type is infecting a culture, it is possible to detect microorganism infection when multiple microorganism types (e.g., multiple microorganism species) infect a single culture.

While numerous exemplary values for novel parameters (e.g., average relative transformation value, extent of growth exhibited by the culture) disclosed herein are given in the data presented herein for detecting whether a culture is infected with microorganisms using a given media, it is to be appreciated that these values for the novel parameters may change when the media used to support growth of the culture is altered. Moreover, it is possible that the values of the novel parameters may vary when a different incubator is used. Thus, preferentially, the same incubator used to generate reference values for the detection of microorganism infection should be used for cultures where the microorganism status is not known. Moreover, the same culture media used to generate reference values for the detection of microorganism infection should be used for cultures where the microorganism status is not known.

In some embodiments, the culture in the vessel is deemed to contain the plurality of microorganisms when an average relative transformation value in the plurality of average relative transformation values exceeds the first threshold value. In some embodiments, the culture in the vessel is deemed to contain the plurality of microorganisms when the extent of growth exhibited by the culture exceeds the second threshold value.

In some embodiments, the method determines that the culture in the vessel contains the plurality of microorganisms and the plurality of microorganisms is bacteria in the Enterobacteriaceae family. In some embodiments, the method determines that the culture contains the plurality of microorganisms, and the plurality of microorganisms in the culture is (i) Enterobacteriaceae, (ii) Staphylococcaceae, (iii) *Streptococcus*, or (iv) *Acinetobacter*. In some embodiments, the method determines that the culture contains the plurality of microorganisms and the plurality of microorganisms are *Alishewanella, Alterococcus, Aquamonas, Aranicola, Arsenophonus, Azotivirga, Blochmannia, Brenneria, Buchnera, Budvicia, Buttiauxella, Cedecea, Citrobacter, Dickeya, Edwardsiella, Enterobacter, Erwinia, Escherichia, Ewingella, Griimontella, Hafnia, Klebsiella, Kluyvera, Leclercia, Leminorella, Moellerella, Morganella, Obesumbacterium, Pantoea, Pectobacterium, Candidatus Phlomobacter, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia*, or *Yokenella*.

In some embodiments, the method determines that the culture in the vessel contains the plurality of microorganisms and the plurality of microorganisms are a single species of Staphylococcaceae selected from the group consisting of *Staphylococcus aureus, Staphylococcus caprae, Staphylococcus epidermidis, Staphylococcus haemolyticus, Staphylococcus hominis, Staphylococcus lugdunensis, Staphylococcus pettenkoferi, Staphylococcus saprophyticus, Staphylococcus warneri*, and *Staphylococcus xylosus*.
In some embodiments, the method determines that the culture contains the plurality of microorganisms and the plurality of microorganisms is *Staphylococcus aureus* or coagulase negative staphylococci. In some embodiments the method determines that the culture contains the plurality of microorganisms and the plurality of microorganisms are a single species of *Streptococcus* selected from the group consisting of *S. agalactiae, S. bovis, S. mutans, S. pneumoniae, S. pyogenes, S. salivarius, S. sanguinis, S. suis, Streptococcus viridans*, and *Streptococcus uberis*.

In some embodiments, the method determines that the culture in the vessel contains the plurality of microorganisms and the plurality of microorganisms is aerobic. In some embodiments, the method determines that the culture in the vessel contains the plurality of microorganisms, and the plurality of microorganisms is anaerobic. In some embodiments, the initial biological state of the culture is measured by a colorimetric means, a fluorometric means, a nephelometric means, or an infrared means. In some embodiments, each biological state in the plurality of measurements of the biological state is determined by a colorimetric means, a fluorometric means, a nephelometric means, or an infrared means. In some embodiments, the culture is a blood culture from a subject.

In some embodiments, only the first result is obtained and used to determine whether the culture in the vessel contains the plurality of organisms. In some embodiments, only the second result is used to determine whether the culture in the vessel contains the plurality of organisms. In some embodiments, the first result and the second result are used to determine whether the culture in the vessel contains the plurality of organisms.

In another aspect, the present invention provides an apparatus for determining whether a culture in a vessel contains a plurality of microorganisms in which the apparatus comprises a processor and a memory, coupled to the processor, for carrying out any of the methods disclosed herein. In still another aspect of the present invention, a computer-readable medium storing a computer program product for determining whether a culture in a vessel contains a plurality of microorganisms, where the computer program product is executable by a computer. The computer program product comprises instructions for carrying out any of the methods disclosed herein.

In another aspect, the present invention provides a method of determining whether a culture in a vessel contains a plurality of microorganisms. The method comprises obtaining a plurality of measurements of the biological state of the culture, each measurement in the plurality of measurements taken at a different time point between a first time point and a second time point. The method further comprises determining, for each respective predetermined fixed interval of time points between the first time point and the second time point, a first derivative of the measurements of the biological state in the respective predetermined fixed interval of time points, thereby forming a plurality of rate transformation values, where the plurality of rate transformation values comprises a plurality of sets of rate transformation values, where each respective set of rate transformation values in the plurality of sets of rate transformation values is for a different set of contiguous time points between the first time point and the second time point. The method further comprises computing, for each respective set of rate transformation values in the plurality of sets of rate transformation values, an average relative transformation value as a measure of central tendency of each of the rate transformation values in the respective set of rate transformation values, thereby computing a plurality of average relative transformation values. The method further comprises obtaining (i) a first result based on a determination of whether any average relative transformation value in the plurality of average relative transformation values exceeds a first threshold value or (ii) a second result based on a determination of whether an extent of growth exhibited by the culture exceeds a second threshold value. The method further comprises using the first result or the second result to determine whether the culture in the vessel contains the plurality of microorganisms.

As such, the systems and methods of the present invention can provide a number of applications useful in microbiology and related fields, and finds particular application in cell culture sterility test procedures.

4 BRIEF DESCRIPTION OF THE DRAWINGS

Like reference numerals refer to corresponding parts throughout the several views of the drawings.

5 DETAILED DESCRIPTION OF THE INVENTION

Figure 1:
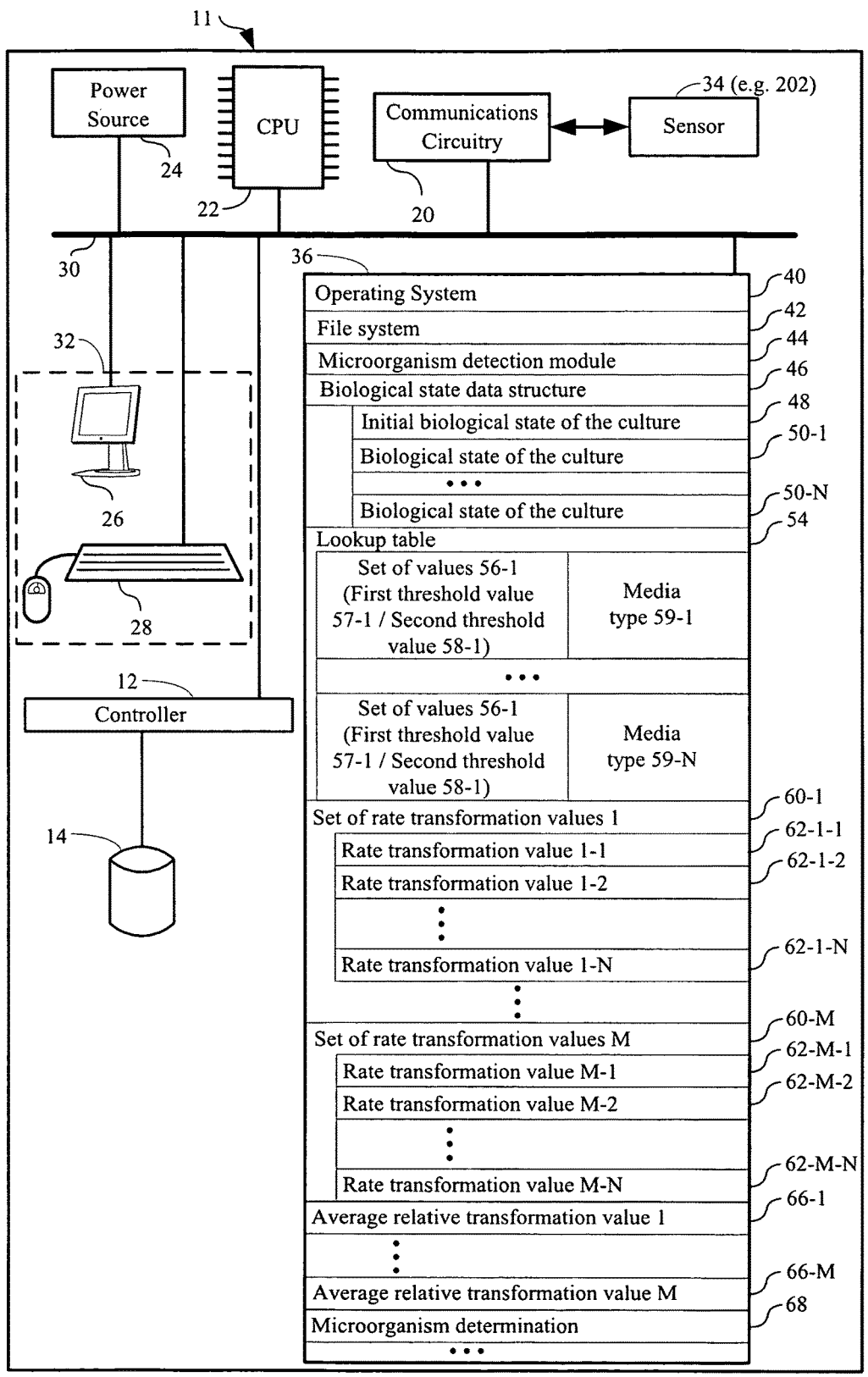
FIG. 1 illustrates an apparatus for determining whether a culture in a vessel contains a plurality of microorganisms, the apparatus comprising a processor and a memory, coupled to the processor, in accordance with an embodiment of the present invention.

Systems, methods, and apparatus for determining whether a culture in a vessel contains a plurality of microorganisms are provided. A normalization relative value is calculated for each respective measurement of a biological state of the culture between (i) the respective measurement and (ii) an initial biological state. For each fixed interval of time points between a first time point and a second time point, a derivative of the normalization relative values for measurements of the biological state in the interval of time points is calculated, thereby forming a plurality of rate transformation values. For each set of rate transformation values in the plurality of rate transformation values, a measure of central tendency of the values in the set is computed, thereby forming a plurality of average relative transformation values. A determination of whether the culture contains the microorganisms is made based on whether any calculated average relative transformation value exceeds a first threshold or whether an extent of growth exhibited by the culture exceeds a second threshold.

One such system in which the present invention can be implemented is the BACTEC® blood culture system. The BACTEC® blood culture system uses fluorescent sensors that report changes to the system when microbial metabolism occurs. Algorithms are then applied to the sequence of signal data that are designed to recognize signal changes with time that are indicative of the presence of growing microorganisms. The user is notified when the system recognizes evidence of growth (status change to a positive vial) and the vessel is then processed to confirm the presence of a microorganism (e.g. using a gram stain and subculture to a plated medium) before initiating processes to begin organism identification and antimicrobial susceptibility determinations.

5.1 Definitions

The term "*Acinetobacter*" as used herein refers to a Gram-negative genus of bacteria belonging to the phylum Proteobacteria. Non-motile, *Acinetobacter* species are oxidase-negative, and occur in pairs under magnification.

The term "biological state" as used herein refers to a measure of the metabolic activity of a culture as determined by, for example, $CO_2$ concentration, $O_2$ concentration, pH, a rate of change in $CO_2$ concentration, a rate of change in $O_2$ concentration, or a rate of change in pH in the culture.

The term "blood" as used herein means either whole blood or any one, two, three, four, five, six, or seven cell types from the group of cells types consisting of red blood cells, platelets, neutrophils, eosinophils, basophils, lymphocytes, and monocytes. Blood can be from any species including, but not limited to, humans, any laboratory animal (e.g., rat, mouse, dog, chimp), or any mammal.

The term "blood culture" as used herein refers to any amount of blood that has been mixed with blood culture media. Examples of culture media include, but are not limited to, supplemented soybean casein broth, soybean casein digest, hemin, menadione, sodium bicarbonate, sodium polyaneltholesulfonate, sucrose, pyridoxal HCKl, yeast extract, and L-cysteine. One or more reagents that may be used as blood culture media are found, for example, in Stanier et al., 1986, *The Microbial World,* 5$^{th}$ edition, Prentice-Hall, Englewood Cliffs, N.J., pages 10-20, 33-37, and 190-195, which is hereby incorporated by reference herein in its entirety for such purpose. In some instances, a blood culture is obtained when a subject has symptoms of a blood infection or bacteremia. Blood is drawn from a subject and put directly into a vessel containing a nutritional culture media. In some embodiments, ten milliliters of blood is needed for each vessel.

The term "culture" as used herein refers to any biological sample from a subject that is either in isolation or mixed with one or more reagents that are designed to culture cells. The biological sample from the subject can be, for example, blood, cells, a cellular extract, cerebral spinal fluid, plasma, serum, saliva, sputum, a tissue specimen, a tissue biopsy, urine, a wound secretion, a sample from an in-dwelling line catheter surface, or a stool specimen. The subject can be a member of any species including, but not limited to, humans, any laboratory animal (e.g., rat, mouse, dog, chimp), or any mammal. One or more reagents that may be mixed with the biological sample are found, for example, in Stanier et al., 1986, *The Microbial World,* 5$^{th}$ edition, Prentice-Hall, Englewood Cliffs, N.J., pages 10-20, 33-37, and 190-195, which is hereby incorporated by reference herein in its entirety for such purpose. A blood culture is an example of a culture. In some embodiments, the biological sample is in liquid form and the amount of the biological sample in the culture is between 1 ml and 150 ml, between 2 ml and 100 ml, between 0.5 ml and 90 ml, between 0.5 ml and 10,000 ml, or between 0.25 ml and 100,000 ml. In some embodiments, the biological sample is in liquid form and is between 1 and 99 percent of the volume of the culture, between 5 and 80 percent of the volume of the culture, between 10 and 75 percent of the volume of the culture, less than 80 percent of the volume of the culture, or greater than 10 percent of the volume of the culture. In some embodiments, the biological sample is between 1 and 99 percent of the total weight of the culture, between 5 and 80 percent of the total weight of the culture, between 10 and 75 percent of the total weight of the culture, less than 80 percent of the total weight of the culture, or greater than 10 percent of the total weight of the culture.

As used herein, the term "Enterobacteriaceae" refers to a large family of bacteria, including *Salmonella* and *Escherichia coli*. Enterobacteriaceae are also referred to herein as the Enteric group. Genetic studies place them among the Proteobacteria, and they are given their own order (Enterobacteriales). Members of the Enterobacteriaceae are rod-shaped, and are typically 1 µm to 5 µm in length. Like other proteobacteria they have Gram-negative stains, and they are facultative anaerobes, fermenting sugars to produce lactic acid and various other end products. They also reduce nitrate to nitrite. Unlike most similar bacteria, Enterobacteriaceae generally lack cytochrome C oxidase, although there are exceptions (e.g. *Plesiomonas*). Most have many flagella, but a few genera are non-motile. They are non-spore forming, and except for *Shigella dysenteriae* strains they are catalase-positive. Many members of this family are a normal part of the gut flora found in the intestines of humans and other animals, while others are found in water or soil, or are parasites on a variety of different animals and plants. Most members of Enterobacteriaceae have peritrichous Type I fimbriae involved in the adhesion of the bacterial cells to their hosts. Genera of the Enterobacteriaceae include, but are not limited to, *Alishewanella, Alterococcus, Aquamonas, Aranicola, Arsenophonus, Azotivirga, Blochmannia, Brenneria, Buchnera, Budvicia, Buttiauxella, Cedecea, Citrobacter, Dickeya, Edwardsiella, Enterobacter, Erwinia* (e.g. *Erwinia amylovora*), *Escherichia* (e.g. *Escherichia coli*), *Ewingella, Griimontella, Hafnia, Klebsiella* (e.g. *Klebsiella pneumoniae*), *Kluyvera, Leclercia, Leminorella, Moellerella, Morganella, Obesumbacterium, Pantoea, Pectobacterium, Candidatus Phlomobacter, Photorhabdus* (e.g., *Photorhabdus luminescens*), *Plesiomonas* (e.g. *Plesiomonas shigelloides*), *Pragia, Proteus* (e.g. *Proteus vulgaris*), *Providencia, Rahnella, Raoultella, Salmonella, Samsonia, Serratia* (e.g. *Serratia marcescens*), *Shigella, Sodalis, Tatumella, Trabulsiella, Wigglesworthia, Xenorhabdus, Yersinia* (e.g., *Yersinia pestis*), and *Yokenella*. More information about Enterobacteriaceae is found in Stanier et al., 1986, *The Microbial World*, 5th edition, Prentice-Hall, Englewood Cliffs, N.J., Chapter 5, which is hereby incorporated by reference herein for such purpose.

As used herein, the term "instance" refers to the execution of a step in an algorithm. Some steps in an algorithm may be run several times, with each repeat of the step being referred to as an instance of the step.

As used herein, the term "microorganism" refers to organisms with a diameter of 1 mm or less excluding viruses.

As used herein, the term "microorganism type" refers to any subclassification of the bacteria kingdom such as a phylum, class, order, family, genus or species in the bacteria kingdom.

As used herein, the term "portion" refers to at least one percent, at least two percent, at least ten percent, at least twenty percent, at least thirty percent, at least fifty percent, as least seventy-five percent, at least ninety percent, or at least 99 percent of a set. Thus, in a nonlimiting example, at least a portion of a plurality of objects means at least one percent, at least two percent, at least ten percent, at least twenty percent, at least thirty percent, at least fifty percent, as least seventy-five percent, at least ninety percent, or at least 99 percent of the objects in the plurality.

As used herein, the term "Staphylococcaceae" refers to a family of bacteria in the Bacillales order that includes, but is not limited to, the *Staphylococcus aureus, Staphylococcus caprae, Staphylococcus epidermidis, Staphylococcus haemolyticus, Staphylococcus hominis, Staphylococcus lugdunensis, Staphylococcus pettenkoferi, Staphylococcus saprophyticus, Staphylococcus warneri*, and *Staphylococcus xylosus* bacteria.

As used herein, the term "*Streptococcus*" refers to a genus of spherical Gram-positive bacteria, belonging to the phylum Firmicutes and the lactic acid bacteria group. Cellular division occurs along a single axis in these bacteria, and thus they grow in chains or pairs, hence the name—from Greek streptos, meaning easily bent or twisted, like a chain. This is contrasted with staphylococci, which divide along multiple axes and generate grape-like clusters of cells. Species of *Streptococcus* include, but are not limited to *S. agalactiae, S. bovis, S. mutans, S. pneumoniae, S. pyogenes, S. salivarius, S. sanguinis, S. suis, Streptococcus viridans*, and *Streptococcus uberis*.

As used herein, a "subject" is an animal, preferably a mammal, more preferably a non-human primate, and most preferably a human. The terms "subject", "individual" and "patient" are used interchangeably herein.

As used herein, the term "vessel" refers to any container that can hold a culture such as a blood culture. For instance, in one embodiment a vessel is a container having a side wall, a bottom wall, an open top end for receiving a culture to be contained within the container, where the container is formed from a material such as glass, clear plastic (e.g., a cyclic olefin copolymer) having a transparency sufficient to visually observe turbidity in the sample, and where the is preferably resistant to heating at a temperature of at least 250° C. In some embodiments, the container has a wall thickness sufficient to withstand an internal pressure of at least 25 psi and a closure coupled to the open end of the container, where the culture is substantially free of contamination after storage in the vessel for an extended period of time under ambient conditions. Exemplary containers are described in U.S. Pat. No. 6,432,697, which is hereby incorporated herein by reference. In some embodiments, the extended period of time under ambient conditions is at least about one year at about 40° C. In some embodiments, the vessel further comprises a fluorescent sensor compound fixed to an inner surface of the container that, when exposed to oxygen, exhibits a reduction in fluorescent intensity upon exposure to a fluorescing light. In some embodiments, the container is substantially transparent to said fluorescing light. In some embodiments, the fluorescent sensor compound comprises at least one compound selected from the group consisting of tris-4,7-diphenyl-1,10-phenanthroline ruthenium (II) salts, tris-2,2'-bipyridyl ruthenium (II) salts, 9,10-diphenyl anthracene, and mixtures thereof. In some embodiments, a vessel is a Blood Culture BACTEC® LYTIC/10 Anaerobic/F culture vial, a BBL® SEPTI-CHEK® vial, a BBL® SEPTI-CHEK® blood culture bottle, a Becton Dickinson BACTEC® vial, a Plus Aerobic/F* and Plus Anaerobic/F* culture vial, a Becton Dickinson BACTEC® Standard/10 Aerobic/F culture vial, a Becton Dickinson BACTEC® Myco/F Lytic culture vial, a Becton Dickinson BACTEC® PEDS PLUS®/F culture vial, or a Becton Dickinson BACTEC® Standard Anaerobic/F culture vial (Becton Dickinson, Franklin Lakes, N.J.).

5.2 Exemplary Apparatus

FIG. 1 details an apparatus 11 for determining whether a culture in a vessel contains a plurality of microorganisms that comprises a processor and a memory, coupled to the processor. The processor and memory illustrated in FIG. 1 can be, for example, part of an automated or semiautomated radiometric or nonradiometric microorganism culture system. The apparatus 11 preferably comprises:

- a central processing unit 22;
- optionally, a main non-volatile storage unit 14, for example a hard disk drive, for storing software and data, the storage unit 14 controlled by storage controller 12;
- a system memory 36, preferably high speed random-access memory (RAM), for storing system control programs, data, and application programs, comprising programs and data (optionally loaded from non-volatile storage unit 14); system memory 36 may also include read-only memory (ROM);
- a user interface 32, comprising one or more input devices (e.g., keyboard 28, a mouse) and a display 26 or other output device;
- a sensor 34 for taking a measurement of a biological state of a culture in a vessel;
- a network interface card 20 (communications circuitry) for connecting to the sensor 34;
- an internal bus 30 for interconnecting the aforementioned elements of the system; and
- a power source 24 to power the aforementioned elements.

Operation of central processing unit 22 is controlled primarily by operating system 40. Operating system 40 can be stored in system memory 36. In a typical implementation, system memory 36 also includes:

- a file system 42 for controlling access to the various files and data structures used by the present invention;
- a microorganism detection module 44 for determining whether a culture in a vessel contains a plurality of microorganisms;
- a biological data structure 46 for storing an initial biological state 48 of the culture and a plurality of measurements of the biological state of the culture, where each measurement 50 in the plurality of measurements is taken at a different time point between a first (initial) time point and a second (final) time point;
- an optional lookup table 54 that comprises matches between (i) a plurality of sets of values, each set of values 56 in the plurality of sets of values comprising a first threshold value 57 and a second threshold value 58, and (ii) a set of media types, wherein, for each set of values 56 in the plurality of sets of values there is corresponding media type 59 in the set of media types;
- sets of rate transformation values 60, where each set of rate transformation values comprises a plurality of rate transformation values 62, where each rate transformation value 62 is a first derivative of the normalization relative values associated with a predetermined fixed interval of time points;
- an average relative transformation value 66 for each set 60 of rate transformation values 60; and
- a data structure for storing a determination 68 of whether a culture in a vessel contains a plurality of microorganisms.

As illustrated in FIG. 1, apparatus 11 can comprise data such as biological state data structure 46, optional lookup table 54, sets of rate transformation values 60, average relative transformation values 66, and a determination 68 of whether a culture in a vessel contains a plurality of microorganisms. In some embodiments, memory 36 or optional data store 14 also stores a measure of central tendency of the average relative transformation values 66. The data described above can be in any form of data storage including, but not limited to, a flat file, a relational database (SQL), or an on-line analytical processing (OLAP) database (MDX and/or variants thereof). In some embodiments, such data structures are stored in a database that comprises a star schema that is not stored as a cube but has dimension tables that define hierarchy. Still further, in some embodiments, such data structures are stored in a database that has hierarchy that is not explicitly broken out in the underlying database or database schema (e.g., dimension tables that are not hierarchically arranged). In some embodiments, such data structures are stored in apparatus 11. In other embodiments, all or a portion of these data structures are hosted on (stored on) one or more computers that are addressable by apparatus 11 across an Internet/network that is not depicted in FIG. 1. In some embodiments, all or a portion of one or more of the program modules depicted in apparatus 11 of FIG. 1, such as microorganism detection module 44 are, in fact, resident on a device (e.g., computer) other than apparatus 11 that is addressable by apparatus 11 across an Internet/network that is not depicted in FIG. 1.

Apparatus 11 determines the metabolic activity of a culture by, for example, $CO_2$ concentration, $O_2$ concentration, pH, a rate of change in $CO_2$ concentration, a rate of change in $O_2$ concentration, or a rate of change in pH in a culture. From this metabolic activity determination, apparatus 11 can identify a microorganism type in the culture. In some embodiments, apparatus 11 accommodates a number of culture vessels and serves as an incubator, agitator, and detection system. These components of apparatus 11 are not depicted in FIG. 1 because the nature of such components will vary widely depending on the exact configuration of apparatus 11. For instance, the number of vessels accommodated by apparatus can range from one vessel to more than 1000 vessels. There can be a sensor associated with each vessel in order to measure the biological state of the culture contained within the vessel. The sensor can be on any location of the vessel and there are a wide range of possible sensors that can be used.

Figure 2:
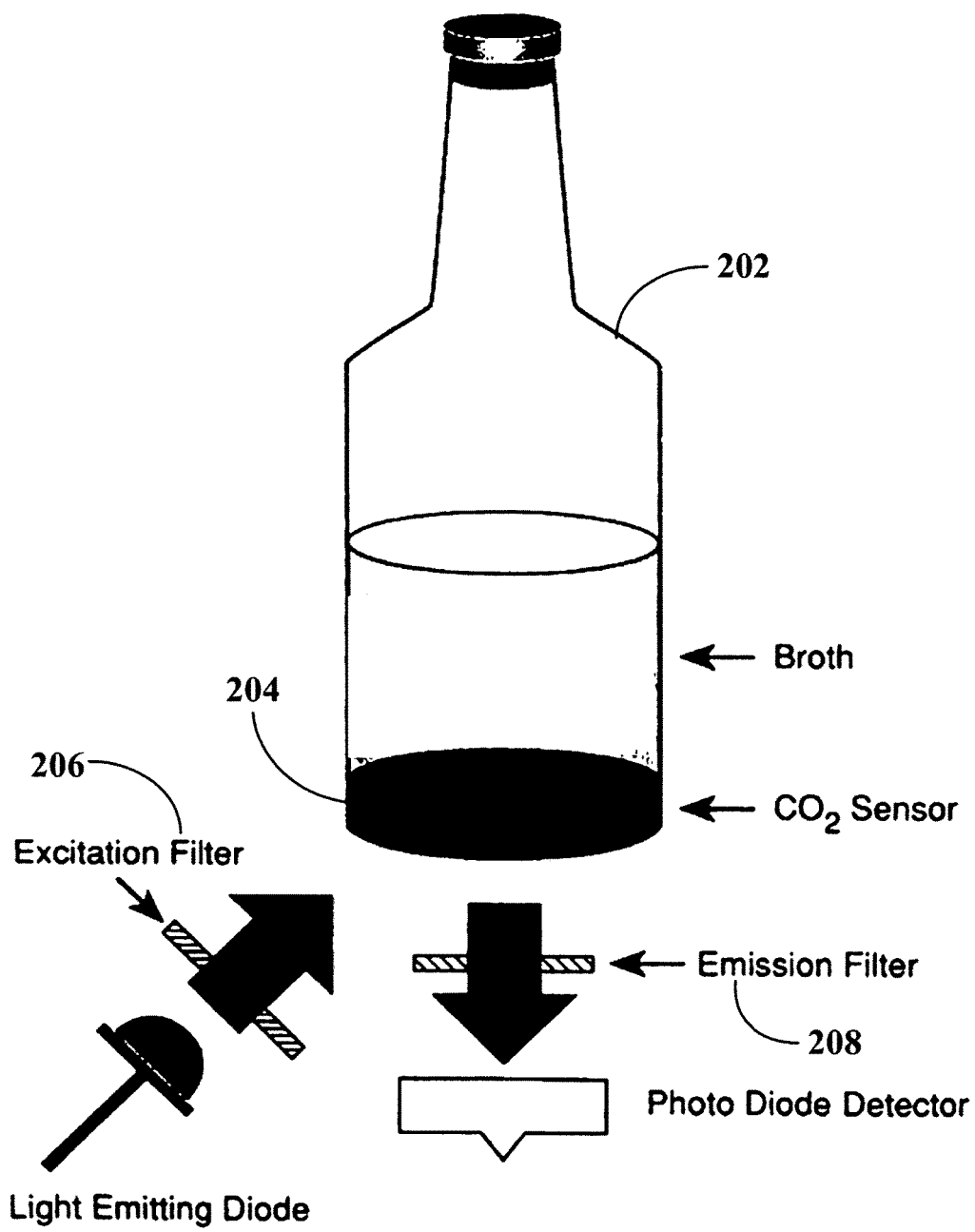
FIG. 2 illustrates a schematic drawing of a culture vessel and $CO_2$ detector system in accordance with an embodiment of the present invention.

FIG. 2 illustrates one exemplary sensor that is capable of measuring the biological state of a culture. In FIG. 2, a $CO_2$ sensor 204 is bonded to the base of culture bottle 202 (vessel) and overlaid with an amount of culture. $CO_2$ sensor 204 is impermeable to ions, medium components, and culture but is freely permeable to $CO_2$. Carbon dioxide produced by the cells in the culture diffuses into sensor 204 and dissolves in the water present in the sensor matrix, generating hydrogen ions. Increases in hydrogen ion concentration (decreases in pH) increase the fluorescence output of sensor 204, thereby changing the signal transmitted from excitation filter 206 to emission filter 208. Apparatus 11 takes repeated measurements of the signal penetrating emission filter 208 over time and uses this data to determine whether the culture contains microorganisms using the algorithms disclosed herein.

In some embodiments, apparatus 11 is an incubator, shaker, and fluorescence detector that will hold between 1 and 1000 culture vessels (e.g., 96, 240 or 384 culture vessels). In some embodiments, the vessels are arranged in racks (e.g., circular or linear racks), each of which has a number of vessel stations. For example, in one specific embodiment, apparatus 11 will hold 240 vessels arranged in six racks, where each rack has 40 vessel stations. In some embodiments, each vessel station in apparatus 11 contains a light-emitting diode and a photo diode detector with appropriate excitation and emission filters (e.g., as illustrated in FIG. 2). In some embodiments, the vessels are rocked and heated at 35±1° C.

5.3 Exemplary Method

Now that an exemplary apparatus in accordance with the present invention has been described, exemplary methods in accordance with the present invention will be detailed. In some embodiments, such methods can be implemented by microorganism detection module 44 of FIG. 1. Referring to step 302 of FIG. 3, an initial biological state of the culture is taken. For example, referring to FIG. 2, in some embodiments, an initial read of detector 204 is made to determine the $CO_2$ concentration in the sensor. In alternative embodiments, an initial $O_2$ concentration, pH or other indicia of the biological state of the culture is read in step 302. In some embodiments, the initial biological state of the culture is determined by a fluorescence output of a sensor (e.g., sensor 204) that is in contact with the culture. In some embodiments, the amount of fluorescence output of the sensor is affected by $CO_2$ concentration in the manner described above in conjunction with FIG. 2. In some embodiments, the amount of fluorescence output of the sensor is affected by $O_2$ concentration, pH, or some other indicia of metabolic state known in the art. In general, any physical observable that is indicative of the metabolic rate of the culture can be measured and stored as the initial state. In some embodiments, this physical observable is the accumulation of molecular products (an example being lipopolysaccharide with Gram negative bacteria), non-molecular physical/chemical changes to the environment related to growth (pressure changes), and/or the production of carbon dioxide or other metabolites that accumulate or the consumption of substrate such as oxygen) or the accumulation of cell material.

In some embodiments, an initial biological state of the blood culture is taken in step 302 using colorimetric means, fluorometric means, nephelometric means, or infrared means. Examples of colorimetric means include, but are not limited to, the use of the colorimetric redox indicators such as resazurine/methylene blue or tetrazolium chloride, or the of p-iodonitrotetrazolium violet compound as disclosed in U.S. Pat. No. 6,617,127 which is hereby incorporated by reference herein in its entirety. Another example of colorimetric means includes the colormetric assay used in Oberoi et al. 2004, "Comparison of rapid colorimetric method with conventional method in the isolation of *mycobacterium tuberculosis*," Indian J Med Microbiol 22:44-46, which is hereby incorporated by reference herein in its entirety. In Oberoi et al., a MB/Bact240 system (Organon Teknika) is loaded with culture vessels. The working principle of this system is based on mycobacterial growth detection by a colorimetric sensor. If the organisms are present, $CO_2$ is produced as the organism metabolizes the substrate glycerol. The color of the gas permeable sensor at the bottom of each culture vessel results in increase of reflectance in the unit, which is monitored by the system using infrared rays. Examples of colorimetric means further include any monitoring of the change in a sensor composition color due to a change in gas composition, such as $CO_2$ concentration, in a vessel resulting from microorganism metabolism.

Examples of fluorometric and colorimetric means are disclosed in U.S. Pat. No. 6,096,272, which is hereby incorporated by reference herein in its entirety, which discloses an instrument system in which a rotating carousel is provided for incubation and indexing, and in which there are multiple light sources each emitting different wavelength light for colorimetric and fluorometric detection. As used herein nephelometric means refers to the measurement of culture turbidity using a nephelometer. A nephelometer is an instrument for measuring suspended particulates in a liquid or gas colloid. It does so by employing a light beam (source beam) and a light detector set to one side (usually 90°) of the source beam. Particle density is then a function of the light reflected into the detector from the particles. To some extent, how much light reflects for a given density of particles is dependent upon properties of the particles such as their shape, color, and reflectivity. Therefore, establishing a working correlation between turbidity and suspended solids (a more useful, but typically more difficult quantification of particulates) must be established independently for each situation.

As used herein, an infrared means for measuring a biological state of a blood culture is any infrared microorganism detection system or method known in the art including, but not limited to, those disclosed U.S. Pat. No. 4,889,992, as well as PCT publication number WO/2006071800, each of which is hereby incorporated by reference herein in its entirety.

In some embodiments the data collected in step 302 and certain subsequent steps is sorted and collected into a database that includes identifying information for the vessels such as the identification of the vessel (e.g., by sequence and accession numbers), a record of the dates of inoculation, an amount of a biological sample in the culture.

In some embodiments, the vessel 202 holding the culture comprises a sensor composition 204 in fluid communication with the culture. In such embodiments, the sensor composition 204 comprises a luminescent compound that exhibits a change in luminescent property, when irradiated with light containing wavelengths that cause the luminescent compound to luminesce, upon exposure to oxygen. The presence of the sensor composition 204 is non-destructive to the blood culture. In such embodiments, the measuring step 302 (and each instance of the measuring step 308) comprises irradiating the sensor composition 202 with light containing wavelengths that cause the luminescent compound to luminesce and observing the luminescent light intensity from the luminescent compound while irradiating the sensor composition with the light. In some embodiments, the luminescent compound is contained within a matrix that is relatively impermeable to water and non-gaseous solutes, but which has a high permeability to oxygen. In some embodiments, the matrix comprises rubber or plastic. More details of sensors in accordance with this embodiment of the present invention are disclosed in U.S. Pat. No. 6,900,030 which is hereby incorporated by reference herein in its entirety.

In optional step 304, the measured initial biological state of the culture upon initialization from step 302 is standardized and stored as the initial biological state of the blood culture 48 (e.g. to one hundred percent or some other predetermined value). This initial biological state, stored as data element 48 in FIG. 1, serves as a reference value against subsequent measurements of the biological state of the blood culture. In some embodiments, step 304 is not performed and the absolute measurements of step 302 are used in the algorithms disclosed herein.

Figure 3A:
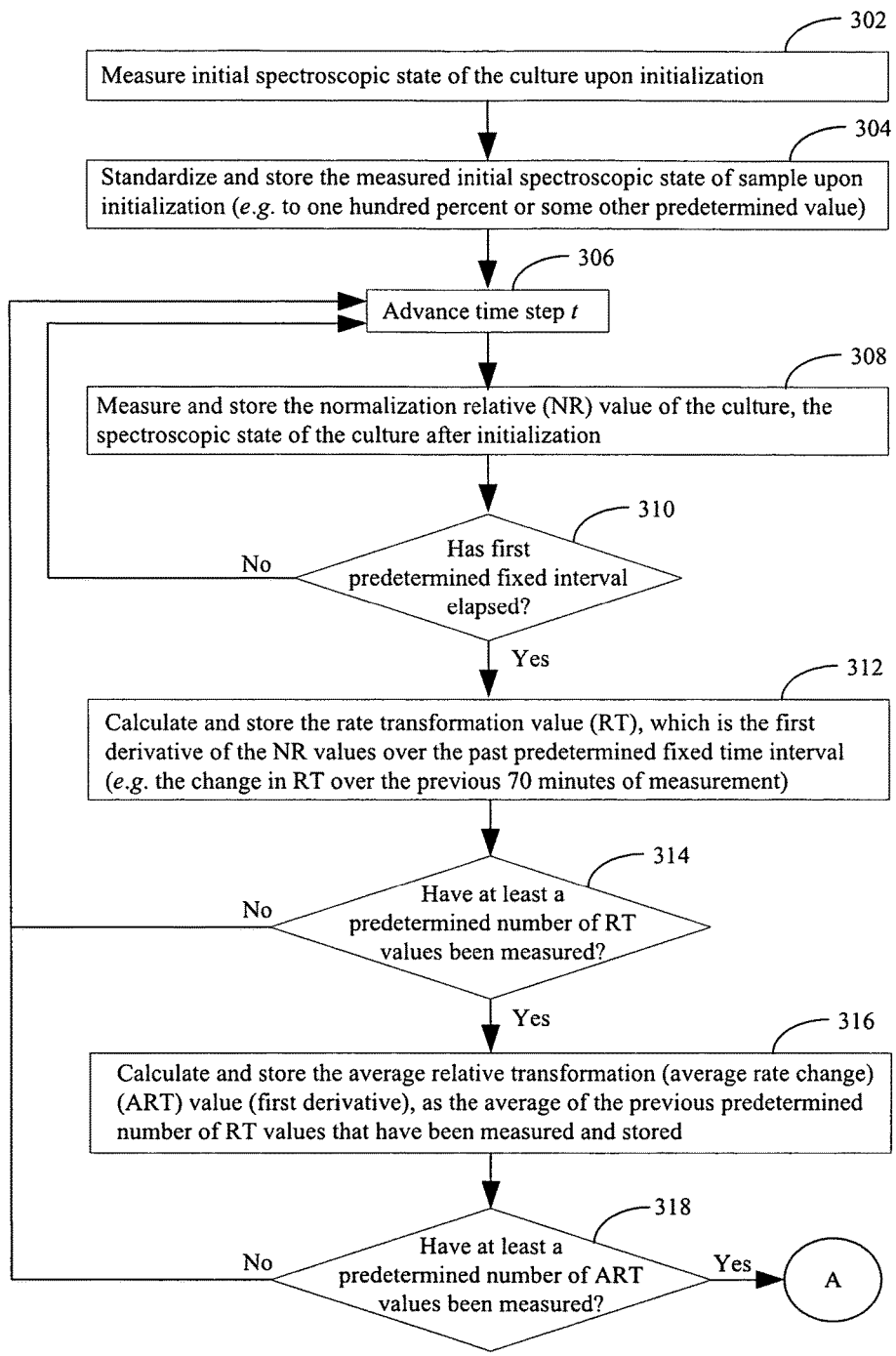
FIGS. 3A & 3B illustrate a method for determining whether a culture in a vessel contains a plurality of microorganisms in accordance with an embodiment of the present invention.

Apparatus 11 incubates the culture for a predetermined period of time after the initial biological state measurement is taken. Then, after the predetermined period of time has elapsed, apparatus 11 makes another measurement of the biological state of the culture. This process is illustrated by steps 306 and 308 in FIG. 3. In FIG. 3A, the process is shown as advancing to time step t in step 306. The biological state during the time period in step 306 in which apparatus waits for time to advance by time step t is not used in subsequent processing steps to ascertain the microorganism type in the culture. In step 308, once time has advanced by time step t, a measurement of the biological state of the culture in the vessel is again taken in the same manner that the initial measurement of the biological state was taken (e.g., using the device depicted in FIG. 2). In some embodiments, the predetermined period of time (the duration of time step t) is ten minutes. In some embodiments, the predetermined period of time (the duration of time step t) is a period of time that is less than 5 minutes, a period of time that is less than 10 minutes, a period of time that is less than 15 minutes, a period of time that is less than 20 minutes, a period of time in the range between 1 minute and 30 minutes, a period of time in the range between 1 minute and 20 minutes, a period of time in the range between 5 minute and 15 minutes, or a period of time that is greater than 5 minutes. The measurement of the biological state of the culture in the vessel taken in step 308 is converted to a normalization relative value by standardizing the measurement of step 308 against the initial measurement of step 302 in embodiments where the initial measurement of step 302 is used for normalization. In one embodiment, the measurement of the biological state of the culture in the vessel taken in step 308 is converted to a normalization relative value by taking the ratio of the measurement of step 308 against the initial measurement of step 302. In some embodiments, this computed normalization relative value is stored as a data element 50 in FIG. 1. In some embodiments, the measurement of the biological state measured in step 308 is stored as a data element 50 in FIG. 1 and the normalization relative value corresponding to the measurement of the biological state measured in step 308 is computed as needed in subsequent processing steps.

In step 310 a determination is made as to whether a first predetermined fixed time interval has elapsed. For example, in some embodiments the predetermined fixed time interval is seventy minutes. In such an example, if the time step t of step 306 is 10 minutes, then it would require time step t to have advanced seven times before condition 310—Yes is achieved. In some embodiments, the predetermined fixed interval of time is a duration of time that is between five minutes and five hours, a duration of time that is between twenty minutes and ten hours, a duration of time that is between twenty minutes and two hours, a duration of time that is between thirty minutes and ninety minutes, a duration of time that is less than 24 hours, or a duration of time that is more than 24 hours. When the first predetermined fixed interval of time has elapsed (310—Yes), process control passes on to step 312 where an additional step of the algorithm is performed. When the first predetermined fixed interval of time has not elapsed (310—No), process control passes back to step 306 where the algorithm waits for time to advance by the amount of time t prior to once again taking a measurement of the biological state of the culture in a new instance of step 308.

The net result of steps 306 through 310 is that a plurality of measurements of a biological state of the culture in the vessel are taken and that each measurement in the plurality of measurements is at a different time point between a first (initial) time point and a terminating (final) time point. Further, in typical embodiments where time step t is the same amount in each instance of step 306, the measurements in the plurality of measurements are each taken of the culture at a periodic interval. In some embodiments, the periodic interval is an amount of time between one minute and twenty minutes, an amount of time between five minutes and fifteen minutes, an amount of time between thirty seconds and five hours, or an amount of time that is greater than one minute.

When a predetermined fixed interval has elapsed (310—Yes), a first derivative of the normalization relative values in the respective predetermined fixed interval (or absolute values from step 302 in the respective predetermined fixed interval in embodiments in which normalization is not performed) is computed in step 312, thereby forming a rate transformation value 62. In other words, the change in the normalization relative values during the predetermined fixed interval is determined in step 312. Note that rate transformation values are the first derivative of normalization relative values in embodiments where measurement data is normalized and rate transformation values are the first derivative of absolute measurements from step 302 in embodiments where measurement data is not normalized. In some embodiments, the predetermined fixed interval of time over which the first derivative is computed is all measurements in an immediately preceding period of time that is between twenty minutes and two hours. For example, in some embodiments the predetermined fixed interval of time of step 310 is seventy minutes and, in step 312, the rate of change across all of the normalization relative values of measurements in this seventy minute time interval (the past 70 minutes) is determined in step 312 and stored as the rate transformation value 62. In some embodiments, the predetermined fixed interval of time over which the first derivative is computed (time window) is all measurements in an immediately preceding period of time that is between five minutes and twenty hours, between thirty minutes and ten hours, between twenty minutes and two hours, between twenty minutes and ten hours, or between thirty minutes and ninety minutes.

In step 314 a determination is made as to whether a predetermined number of rate transformation values have been measured since the last time condition 314—Yes was reached. If so (314—Yes), process control passes on to step 316. If not (314—No), process control returns back to step 306 where process control waits until time step t has elapsed before continuing to step 308 where the normalization relative value of the culture is once again calculated. Each instance of condition (314—Yes) marks the completion of a set 60 of rate transformation values 62. For example, in some embodiments, condition 314—Yes is achieved when seven new rate transformation values 62 have been measured. In this example, a set 60 of rate transformation values comprises or consists of the seven rate transformation values 62. In some embodiments, each set 60 of rate transformation values 62 comprise or consists of between four and twenty contiguous rate transformation values. Contiguous rate transformation values 62 are rate transformation values in the same set 60. Such rate transformation values 62 are, for example, calculated and stored in successive instances of step 312. In some embodiments, each set 60 of rate transformation values 62 in the plurality of rate transformation values comprises or consists of between five and fifteen contiguous rate transformation values 62, between one and one hundred contiguous rate transformation values 62, between five and one fifteen contiguous rate transformation values 62, more than five rate transformation values 62, or less than ten rate transformation values 62.

When condition 314—Yes is achieved, step 316 is run. In step 316, an average relative transformation (average rate of change) value 66 is computed from the newly formed set 60 of rate transformation values 62. Thus, for each set 60 of rate transformation values 62, there is an average relative transformation value 66. In some embodiments, an average relative transformation (average rate of change) value 66 is computed from the newly formed set 60 of rate transformation values 62 by taking a measure of central tendency of the rate transformation values 62 in the newly formed set 60 of rate transformation values 62. In some embodiments, this measure of central tendency is a geometric mean, an arithmetic mean, a median, or a mode of all or a portion of the rate transformation values 62 in the newly formed set 60 of rate transformation values 62.

In step 318, a determination is made as to whether a predetermined point in the protocol has been reached. This predetermined point is a final time point, also known as an end point. In some embodiments, the final time point is reached (318—Yes) one or more hours, two or more hours, ten or more hours, between three hours and one hundred hours, or less than twenty hours after the initial measurement in step 302 was taken. In some embodiments, the final time point is reached (318—Yes) when between 10 and 50,000, between 100 and 10,000, or 150 and 5,000, more than 10, more than fifty, or more than 100 measurements of the biological state of the culture in the vessel have been made in instances of step 308. If the predetermined point in the protocol has not been reached (318—No), then process control returns to step 306 where the process control waits for time step t to advance before initiating another instance of step 308 in which the biological state of the culture is again measured and used to calculate a normalization relative value. If the predetermined point in the protocol has been reached (318—Yes), process control passes to either (i) step 320a, (ii) step 320b, or (iii) both step 320a and step 320b.

In step 320a, a first result is obtained based on a determination of whether any average relative transformation value 66 in the plurality of average relative transformation values exceeds first threshold value 57. In some embodiments, the first threshold value 57 is media type dependent meaning that the exact value for the first threshold value will depend on the media type that was used for the culture. In practice, for example, optional lookup table 54 may store several different first threshold values 57 for several different media types 59. Thus, in step 320a, the optional lookup table 54 is consulted, based on the exact media type 59 of the culture, to determine the correct first threshold value 57 to use. In some embodiments, it is expected that, regardless of the exact media type 59 used, the first threshold value will be in the range of between 50 and 200. In some embodiments, it is expected that, regardless of the exact media type 59 used, the first threshold value will be in the range of between 75 and 125. In some embodiments, it is expected that, regardless of the exact media type 59 used, the first threshold value will be in the range of between 85 and 115. In some embodiments, it is expected that, regardless of the exact media type 59 used, the first threshold value will be in the range of between 95 and 105. If any average relative transformation value 66 in the plurality of average relative transformation values exceeds first threshold value 57 (320a—Yes), then the culture is marked positive for microbial infection (step 322). If none of the average relative transformation values 66 in the plurality of average relative transformation values exceeds the first threshold value 57 (320a—No), then the culture is not marked positive for microbial infection (step 324). However, in some embodiments, even if the condition 320a—No is achieved, other microbial detection algorithms in apparatus 11 may mark the culture as positive for microbial infection. For instance, in some embodiments, step 320b is run and step 320b is capable of marking the culture positive for microbial infection. Furthermore, other additional microbial detection algorithms may be run by apparatus 11 on the culture, for example an algorithm that detects an inflection point in the rate of acceleration of a signal from the culture, and these other additional microbial detection algorithms may independently determine that the culture is infected with a microorganism.

In step 320b, a second result is obtained based on a determination of whether the extent of growth exhibited by the culture exceeds second threshold value 58. In some embodiments, the second threshold value 58 is media type dependent meaning that the exact value for the second threshold value will depend on the media type that was used for the culture. In practice, for example, lookup table 54 may store several different second threshold values 58 for several different media types 59. Thus, in step 320a, the lookup table 54 is consulted, based on the exact media type 59 of the culture, to determine the correct second threshold value 57 to use. If the extent of growth exceeds the second threshold value 58 (320b—Yes), then the culture is marked positive for microbial infection (step 322). If the extent of growth does not exceed the second threshold value 58, then the culture is not marked positive for microbial infection (step 324). However, in some embodiments, even if the condition 320b—No is achieved, other microbial detection algorithms in apparatus 11 may mark the culture as positive for microbial infection. For instance, in some embodiments, step 320a is run and step 320a is capable of marking the culture positive for microbial infection as described above. Furthermore, other additional microbial detection algorithms may be run by apparatus 11 on the culture, for example an algorithm that detects an inflection point in the rate of acceleration of a signal from the culture, and these other additional microbial detection algorithms may independently determine that the culture is infected with a microorganism.

In some embodiments, the extent of growth (EG) 58 is the maximum normalization relative value measured for the culture. In some embodiments where EG is the maximum normalization relative value, it is expected that, regardless of the exact media type 59 used, the second threshold value will be in the range of between 112 and 140. In some embodiments where EG is the maximum normalization relative value, it is expected that, regardless of the exact media type 59 used, the second threshold value will be in the range of between 113 and 118. In some embodiments where EG is the maximum normalization relative value, it is expected that the second threshold value will be 117.

In some embodiments, the extent of growth is determined by the equation:

$$EG = NR_{after\_growth} - NR_{minimum\_growth} \qquad \text{Eq. 1}$$

where $NR_{after\_growth}$ is a normalization relative value in the plurality of normalization relative values that was used in the calculation of (i) the first average relative transformation value following a maximum average relative transformation value, (ii) a maximum average relative transformation value, or (iii) a first average relative transformation value preceding the maximum average relative transformation value in the plurality of average relative transformation values, and $NR_{minimum\_growth}$ is a normalization relative value in the plurality of normalization relative values that was used in the calculation of the first average relative transformation value to achieve a third threshold value. In some embodiments where EG is defined by Equation 1, the second threshold value will be in the range of between 12 and 40 regardless of the exact media type 59 used. In some embodiments where EG is defined by Equation 1, the second threshold value will be in the range of between 13 and 18 regardless of the exact media type 59 used. In some embodiments where EG is defined by Equation 1, the second threshold value will be 17 regardless of the exact media type 59 used.

In some embodiments, $NR_{after\_growth}$ of Eq. 1 is a normalization relative value in the plurality of normalization relative values that was used in the calculation of the average relative transformation value 66 following the maximum average relative transformation value 66 ever achieved for the culture. Thus, if normalization relative values 145 through 154 were used to compute the average relative transformation value 66 following the maximum average relative transformation value 66, then $NR_{after\_growth}$ would be one of the normalization relative values in the set of normalization relative values {145, ..., 154}.

In some embodiments, $NR_{after\_growth}$ of Eq. 1 is a normalization relative value in the plurality of normalization relative values that was used in the calculation of the average relative transformation value 66 preceding the maximum average relative transformation value 66 ever achieved for the culture. Thus, if normalization relative values 125 through 134 were used to compute the average relative transformation value 66 immediately preceding the maximum average relative transformation value 66, then $NR_{after\_growth}$ would be one of the normalization relative values in the set of normalization relative values {125, ..., 134}.

In some embodiments, $NR_{after\_growth}$ of Eq. 1 is a measure of central tendency of all or a portion of the normalization relative values that were used in the calculation of the maximum average relative transformation value 66 ever achieved for the culture. Thus, if normalization relative values 135 through 144 were used to compute the maximum average relative transformation value 66, then $NR_{after\_growth}$ would be a measure of central tendency (geometric mean, an arithmetic mean, a median, or a mode) of all or a portion of the normalization relative values in the set of normalization relative values {135, ..., 144}.

In some embodiments, $NR_{after\_growth}$ of Eq. 1 is a measure of central tendency of all or a portion of the normalization relative values that were used in the calculation of the average relative transformation value 66 following the maximum average relative transformation value 66 ever achieved for the culture. Thus, if normalization relative values 145 through 154 were used to compute the average relative transformation value 66 following the maximum average relative transformation value 66, then $NR_{after\_growth}$ would be a measure of central tendency (geometric mean, an arithmetic mean, a median, or a mode) of all or a portion of the normalization relative values in the set of normalization relative values {145, ..., 154}.

In some embodiments, $NR_{after\_growth}$ of Eq. 1 is a measure of central tendency of all or a portion of the normalization relative values that were used in the calculation of the average relative transformation value 66 preceding the maximum average relative transformation value 66 ever achieved for the culture. Thus, if normalization relative values 125 through 134 were used to compute the average relative transformation value 66 immediately preceding the maximum average relative transformation value 66, then $NR_{after\_growth}$ would be a measure of central tendency (geometric mean, an arithmetic mean, a median, or a mode) of all or a portion of the normalization relative values in the set of normalization relative values {125, ..., 134}.

In some embodiments, $NR_{minimum\_growth}$ is a normalization relative value in the plurality of normalization relative values that was used in the calculation of the first average relative transformation value 66 to achieve a threshold value. Thus, if normalization relative values 20 through 29 were used to compute the first average relative transformation value 66 to achieve a threshold value, then $NR_{minimum\_growth}$ would be one of the normalization relative values in the set of normalization relative values {20, ..., 29}.

In some embodiments, $NR_{minimum\_growth}$ is a measure of central tendency of the normalization relative values that were used in the calculation of the first average relative transformation value 66 to achieve a threshold value. Thus, if normalization relative values 20 through 29 were used to compute the first average relative transformation value 66 to achieve a threshold value, then $NR_{minimum\_growth}$ would be all or a portion of the normalization relative values in the set of normalization relative values {20, ..., 29}.

In some embodiments, where Equation 1 is used to calculate extent of growth 58, the threshold value is, in nonlimiting examples, a value between 5 and 100, a value between 25 and 75, a value between 1 and 1000, or a value that is less than 50.

In some embodiments, the extent of growth is determined by the equation:

$$EG=NR_{max}-NR_{initial} \qquad \text{Eq. 2}$$

where $NR_{max}$ is the maximum normalization relative value in the plurality of normalization relative values and $NR_{initial}$ is a value of the initial biological state of the culture against which each normalization relative value has been standardized against. In some embodiments where EG is defined by Equation 2, the second threshold value will be in the range of between 12 and 40 regardless of the exact media type 59 used. In some embodiments where EG is defined by Equation 2, the second threshold value will be in the range of between 13 and 18 regardless of the exact media type 59 used. In some embodiments where EG is defined by Equation 2, the second threshold value will be 17 regardless of the exact media type 59 used.

It will be appreciated that equations 1 and 2 can contain additional mathematical operations, both linear and nonlinear, and still be used to compute the extent of growth 58.

In some embodiments, the culture is identified as containing microorganisms when it contains (i) a bacterium in the Enterobacteriaceae family or (ii) a bacterium not in the Enterobacteriaceae family. In some embodiments, the culture is identified as containing microorganisms when it contains (i) Enterobacteriacea, (ii) Staphylococcaceae, (iii) *Streptococcus*, or (iv) *Acinetobacter*. In some embodiments, the culture is identified as containing microorganisms when it contains *Alishewanella, Alterococcus, Aquamonas, Aranicola, Arsenophonus, Azotivirga, Blochmannia, Brenneria, Buchnera, Budvicia, Buttiauxella, Cedecea, Citrobacter, Dickeya, Edwardsiella, Enterobacter, Erwinia, Escherichia, Ewingella, Griimontella, Hafnia, Klebsiella, Kluyvera, Leclercia, Leminorella, Moellerella, Morganella, Obesumbacterium, Pantoea, Pectobacterium, Candidatus Phlomo-*

*bacter, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia,* or *Yokenella.*

In some embodiments, the culture is identified as containing microorganisms when it contains *Staphylococcus aureus, Staphylococcus caprae, Staphylococcus epidermidis, Staphylococcus haemolyticus, Staphylococcus hominis, Staphylococcus lugdunensis, Staphylococcus pettenkoferi, Staphylococcus saprophyticus, Staphylococcus warneri,* or *Staphylococcus xylosus* bacteria. In some embodiments, the culture is identified as containing microorganisms when it contains *S. agalactiae, S. bovis, S. mutans, S. pneumoniae, S. pyogenes, S. salivarius, S. sanguinis, S. suis, Streptococcus viridans,* or *Streptococcus uberis.*

In some embodiments, the culture is identified as containing microorganisms when it contains aerobic bacteria. In some embodiments, the culture is identified as containing microorganisms when it contains anaerobic bacteria.

In some embodiments, the method further comprises outputting the first result (the yes or no condition reached in step 320a), the second result (the yes or no condition reached in step 32b), or a determination of whether the culture in the vessel contains the plurality of microorganisms to a user interface device (e.g., 32), a monitor (e.g., 26), a computer-readable storage medium (e.g., 14 or 36), a computer-readable memory (e.g., 14 or 36), or a local or remote computer system. In some embodiments the first result, the second result, or the determination of whether the culture in the vessel contains the plurality of microorganisms is displayed. As used herein, the term local computer system means a computer system that is directly connected to apparatus 11. As used herein, the term remote computer system means a computer system that is connected to apparatus 11 by a network such as the Internet.

5.4 Exemplary Computer Program Products and Computers

The present invention can be implemented as a computer program product that comprises a computer program mechanism embedded in a computer-readable storage medium. Further, any of the methods of the present invention can be implemented in one or more computers. Further still, any of the methods of the present invention can be implemented in one or more computer program products. Some embodiments of the present invention provide a computer program product that encodes any or all of the methods disclosed herein. Such methods can be stored on a CD-ROM, DVD, magnetic disk storage product, or any other computer-readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise.

Some embodiments of the present invention provide a computer program product that contains any or all of the program modules and data structures shown in FIG. 1. These program modules can be stored on a CD-ROM, DVD, magnetic disk storage product, or any other computer-readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise.

5.5 Kits

Some embodiments of the invention may also comprise a kit to perform any of the methods described herein. In a non-limiting example, vessels, culture for a sample, additional agents, and software for performing any combination of the methods disclosed herein may be comprised in a kit. The kits will thus comprise one or more of these reagents in suitable container means.

The components of the kits, other than the software, vessels, and the radiometric or nonradiometric system, may be packaged either in aqueous media or in lyophilized form. The suitable container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be in a vial. The kits of the present invention also will typically include a means for containing the reagent containers in close confinement for commercial sale. Such containers may include injection or blow-molded plastic containers into which the desired vials are retained.

6 EXAMPLE

A method was developed that allows an increased confidence level in the notification of vessel positive status in a blood culture system. The method set forth herein exemplifies use of this method in the BACTEC® Blood culture system. The BACTEC® Blood culture system uses fluorescent sensors that report changes to the system when microbial metabolism occurs. Algorithms are then applied to the sequence of signal data that are designed to recognize signal changes with time that are indicative of the presence of growing microorganisms. The user is notified when the system recognizes evidence of growth (status change to a positive vial) and the vessel is then processed to confirm the presence of an organism (Gram stain and subculture to a plated medium) before initiating processes to begin organism identification and antimicrobial susceptibility determinations. The prior art system reports a status of presumptive positive as the system has no way of quantifying confidence in the positive determination. The present invention described here utilized the difference in rate of metabolic change and extent of change to provide information about the confidence in a positive status change on an individual vessel basis. The inventive data transformation can be applied to metabolic or cell growth data in a way that provides confidence in the positive status of a vessel and essentially eliminates the potential for false negative determinations as they currently exist in blood culture systems.

Figure 3B:
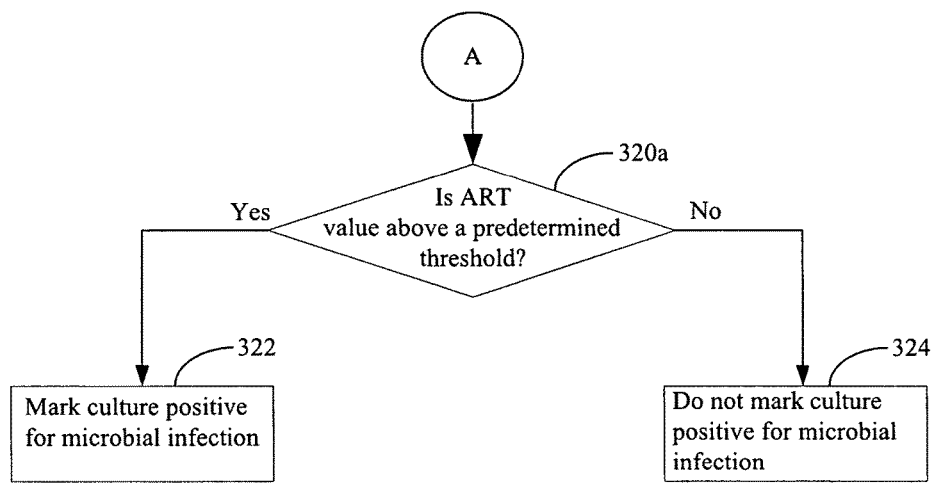
Figure 3B:
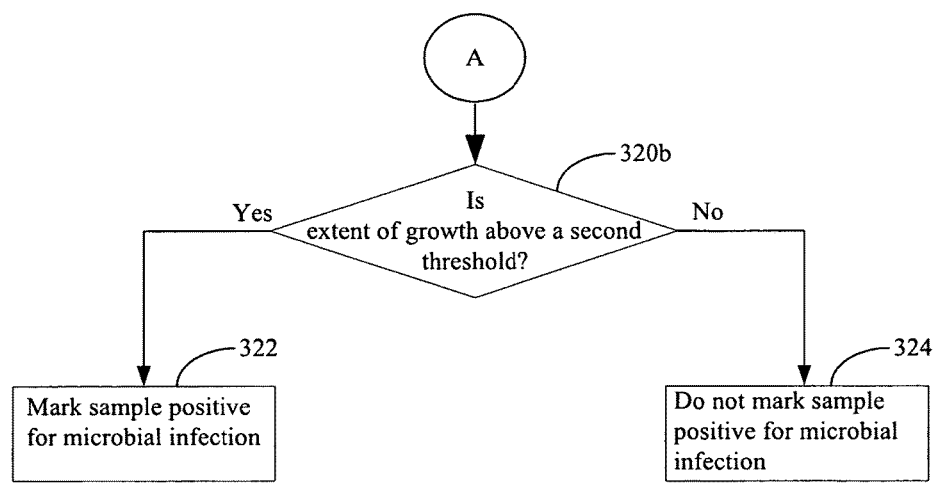

Data that was collected with the BACTEC® blood culture system is used as an example of the application of the inventive data transformation illustrated in FIG. 3 and provided examples of the utility of the present invention. The BACTEC® system, as described above, uses fluorescent sensors to monitor the changes in metabolic activity within the culture through a stream of compensated fluorescence signal data that is collected at ten minute intervals from a sensor located inside the culture reagent. The data used in this example was collected from the BACTEC® instruments used either in internal seeded culture studies or collected during a clinical evaluation of the system. The data was sorted and collected into a database at Becton Dickinson that includes the identification of the vessel (by sequence and accession numbers), a record of the dates of inoculation, the amount of blood in the sample (it is a blood culture system) and the result with the identification of the microorganism found in the vessel (the organism identification was provided by the clinical site in the case of the external data). The algorithm illustrated in FIG. 3 was applied subsequently for analysis. The utility of this information is for determining whether a culture in a vessel contains a plurality of microorganisms The inventive data transformations began with an initial normalization of the vessel signal to a specific output (its initial state upon entering the system), as described above in conjunction with steps 302 and 304 of FIG. 3. All subsequent data was represented as a percentage of that initial signal, which has been standardized to 100 percent in these analyses, as outlined in steps 306 and 308 of FIG. 3. Data measurements normalized by the initial signal were termed normalization relative values. Under ideal theoretical conditions, a normalization relative value of 125 means that microorganism metabolism caused the fluorescence measured by the BACTEC® sensor to increase by 25 percent relative to the initial measurement. The next value that was computed was the first derivative of the NR value as it changes with time as outlined in steps 310 and 312 of FIG. 3. This value was the rate transformation (RT) value and the base RT value used in this example uses a periodicity limit of 70 minutes. Any given RT value represented the rate of percentage change of fluorescence signal over the seventy minutes prior to its calculation. The next value that was computed was the ART or average rate change value as outlined in steps 314 and 316 of FIG. 3. This was calculated as the average of the previous 7 average rate change value (ART) values that had been calculated and acted as a smoothing function of the RT value.

Figure 4:
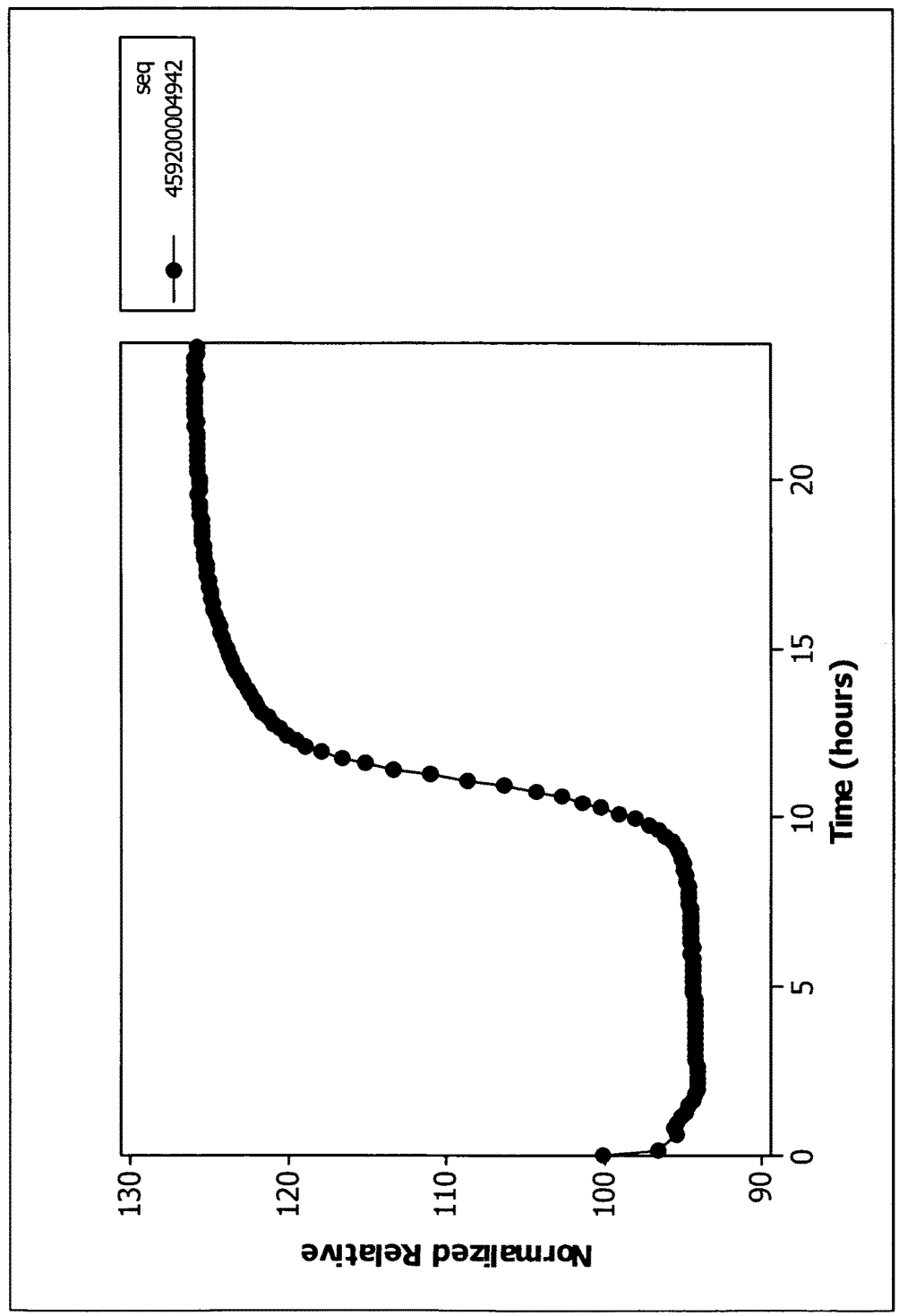
FIG. 4 shows a plot of normalization relative values measured from a blood culture in a vessel in accordance with an embodiment of the present invention.
Figure 5:
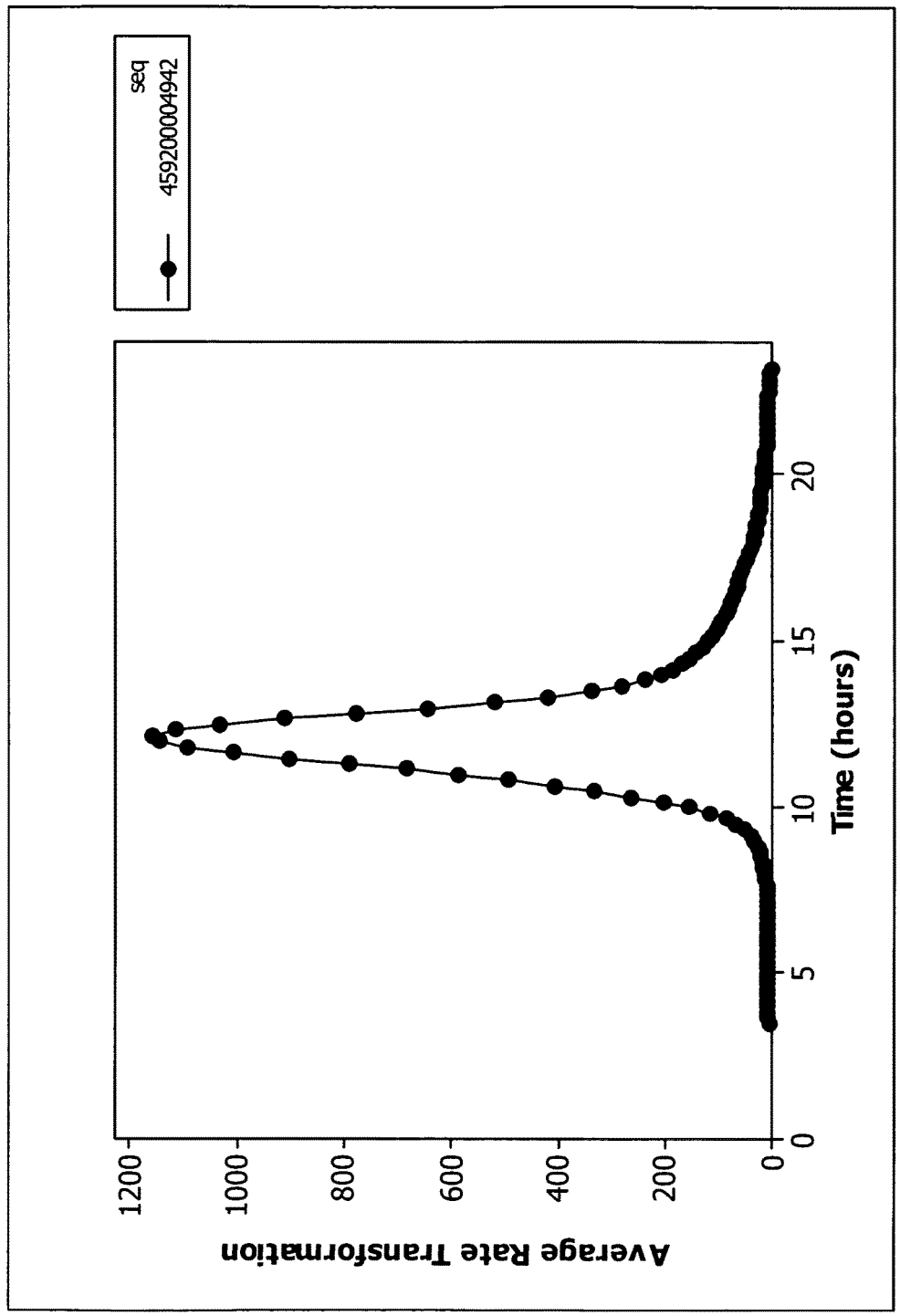
FIG. 5 is a plot of the average relative transformation values over time based on the average rate of change in rate transformation values of FIG. 4 over time in accordance with an embodiment of the present invention.
Figure 6:
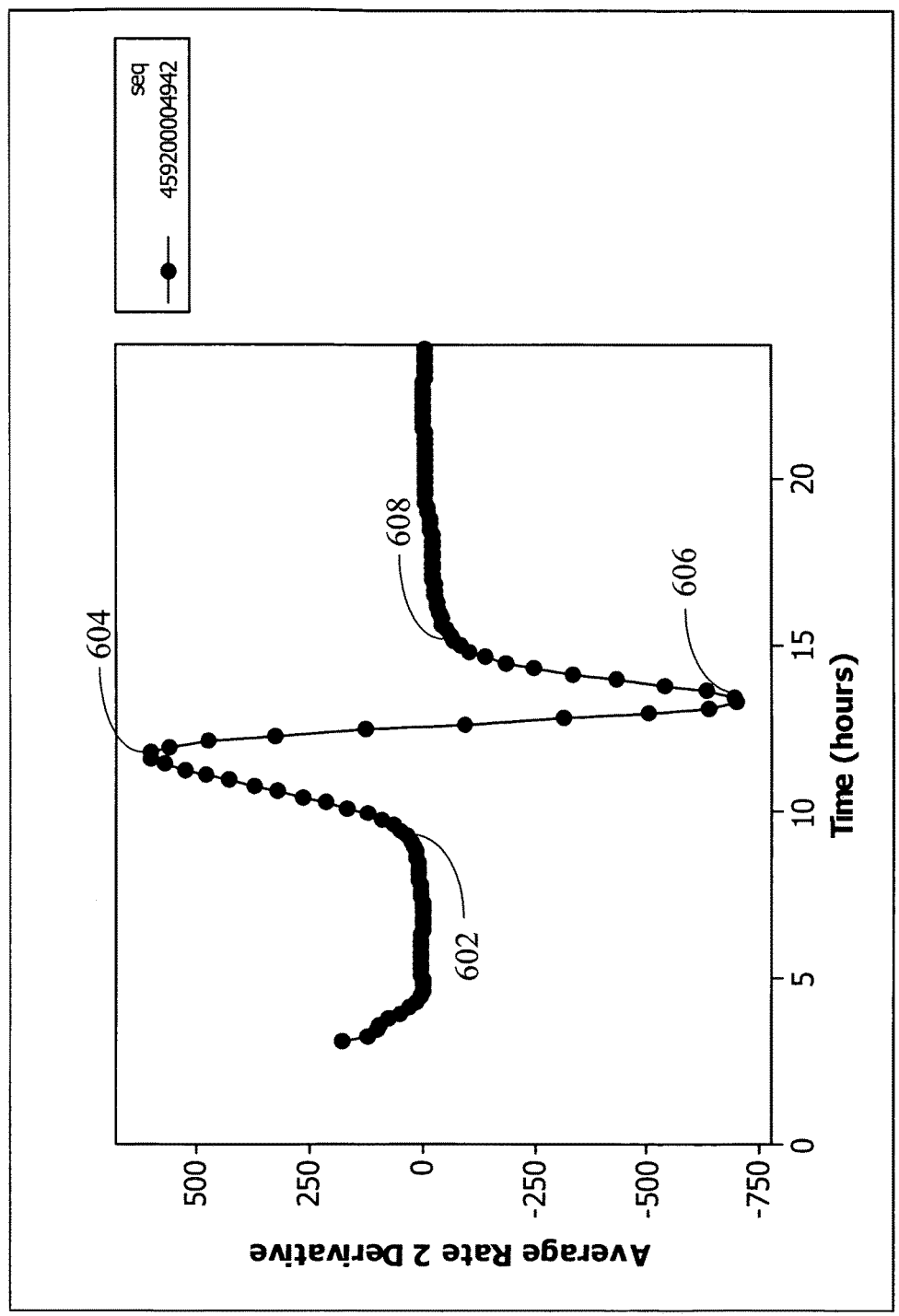
FIG. 6 is the second derivative plot of normalization relative values of FIG. 4 and shows the changes in metabolism rate with time in accordance with an embodiment of the present invention.

Examples of the parameters that were computed to determine whether a culture was infected with microorganisms are presented in FIGS. 4, 5 and 6. An *Escherichia coli* culture was analyzed using these quantitative metrics (the normalized relative values 50, the rate transformation values 62, and the average relative transformation values 66). The culture contained three milliliters of human blood from a subject and was inoculated with a suspension of *E. coli* (55 CFU) and entered into a BACTEC® 9000 instrument. The identifier 4942 uniquely identifies the culture that is reported in FIGS. 4, 5, and 6 and can be used to link the data to a research and development BACTEC® database. FIG. 4 shows a plot of normalization relative values over time. The vessel was entered into the instrument and temperature affects related to equilibration of the vessel were observed for approximately the first hour. The signal stabilized and a background was observed to increase from 94 percent to 95 percent of the initial signal for the first hour (this rate was due to blood activity). In the normalization relative plot (FIG. 4), growth was visible beginning at eight hours and proceeded until 15 hours with a final value NR value near 126. The plot of average relative transformation values 66 over time based on the average rate of change in rate transformation values 62 of FIG. 4 over time is provided in FIG. 5. Each average relative transformation (ART) value 66 is a measure of the average rate of change and the maximum ART for this culture was 1158 achieved at 12.8 hours into the culture. This represents this culture's averaged maximum achieved rate of sensor change over a one hour period. FIG. 6 is the second derivative plot of normalization relative values 50 and shows the changes in rate with time. This is a graphical interpretation showing the following critical points: the point of initial acceleration 602 (movement from the null), the point of maximum acceleration 604 (the maxima), where acceleration reaches its maximum (crossing the null point), the maximum point of deceleration (the minima) 606, and the terminus of the growth curve 608 (where the rate change returns to null).

Figure 7:
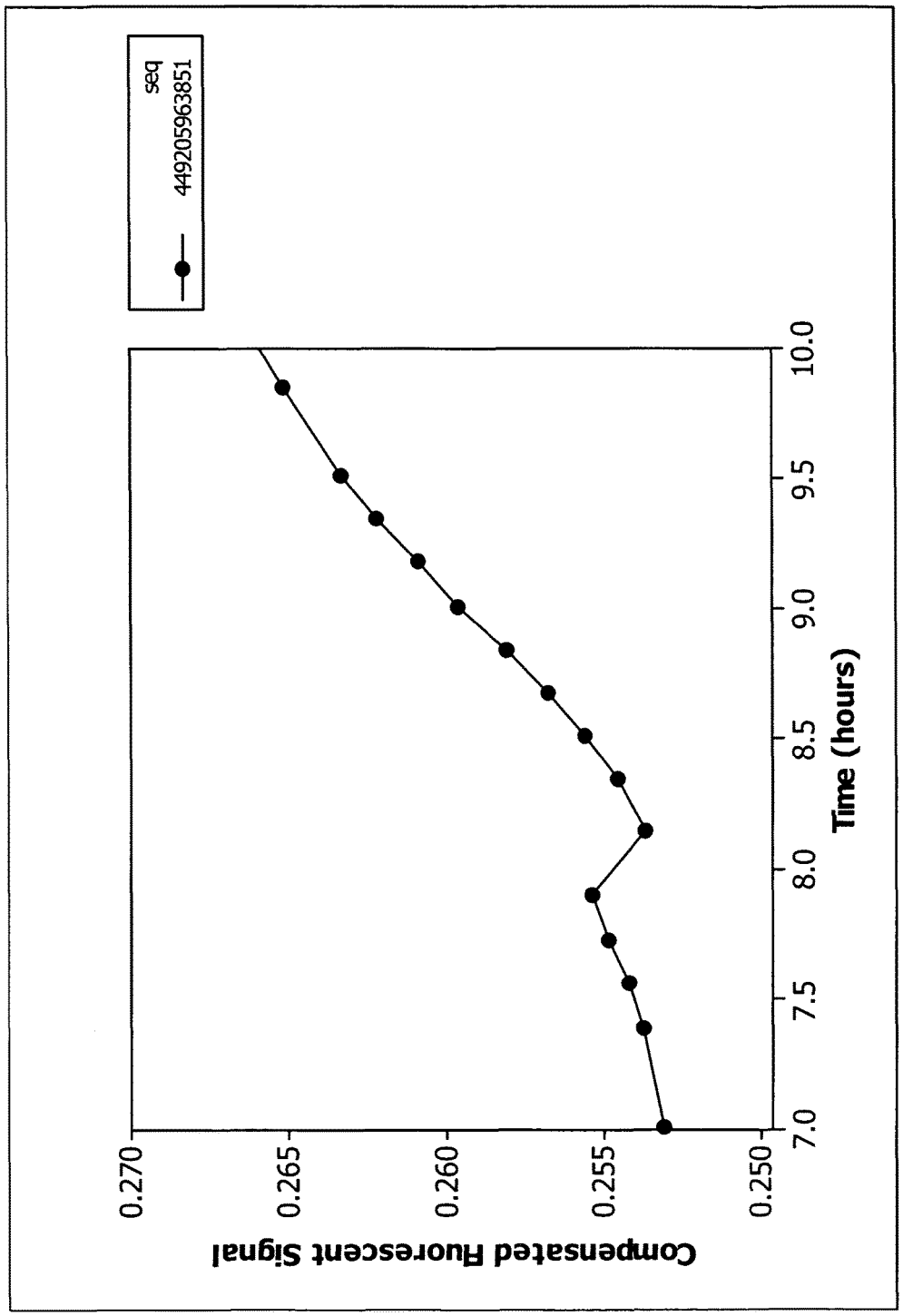
FIG. 7 is a plot of compensated fluorescent signal versus time for a clinical *Enterococcus faecalis* false negative.
Figure 8:
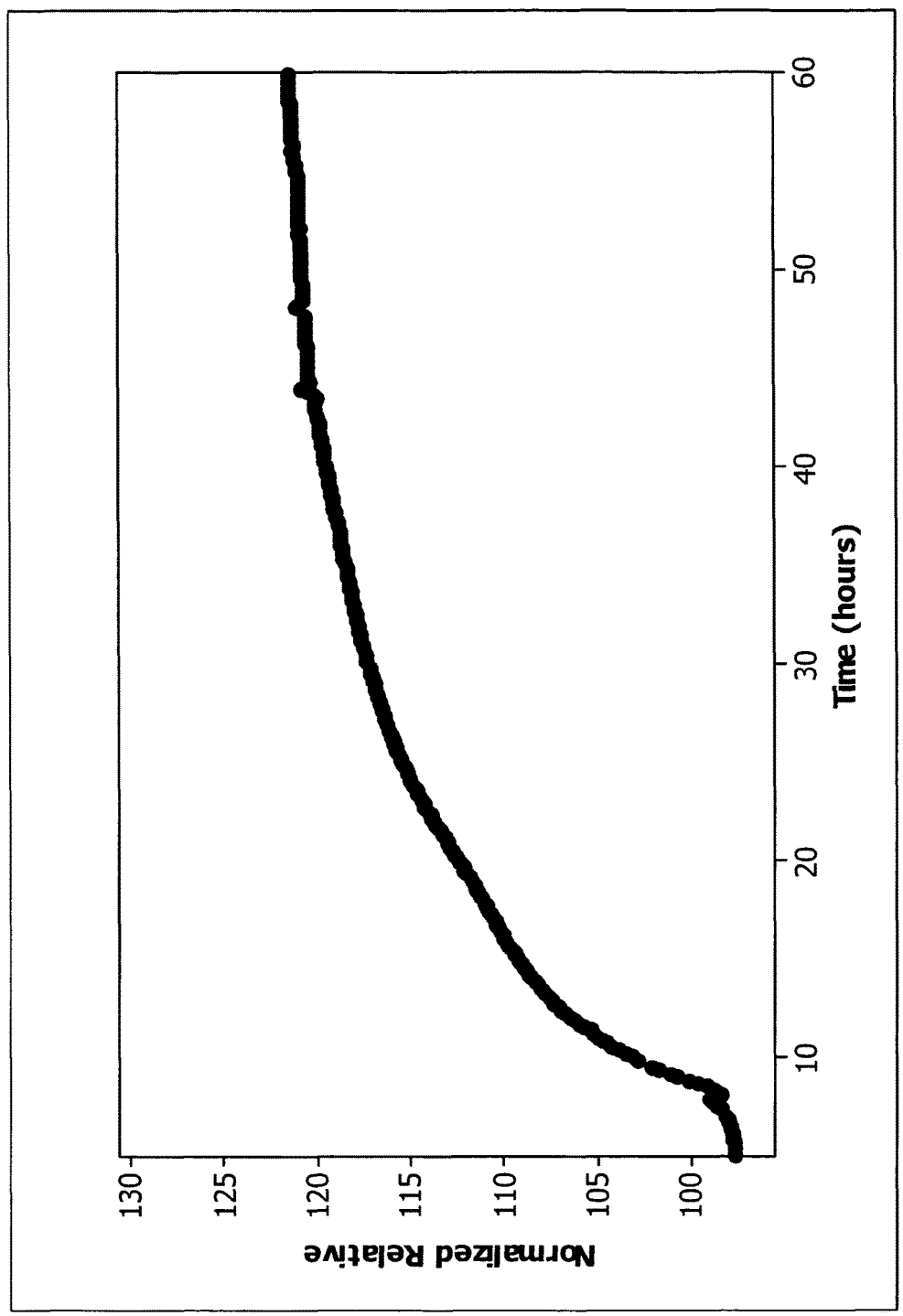
FIG. 8 is a plot of normalized relative values versus time for a clinical *Enterococcus faecalis* false negative.
Figure 9:
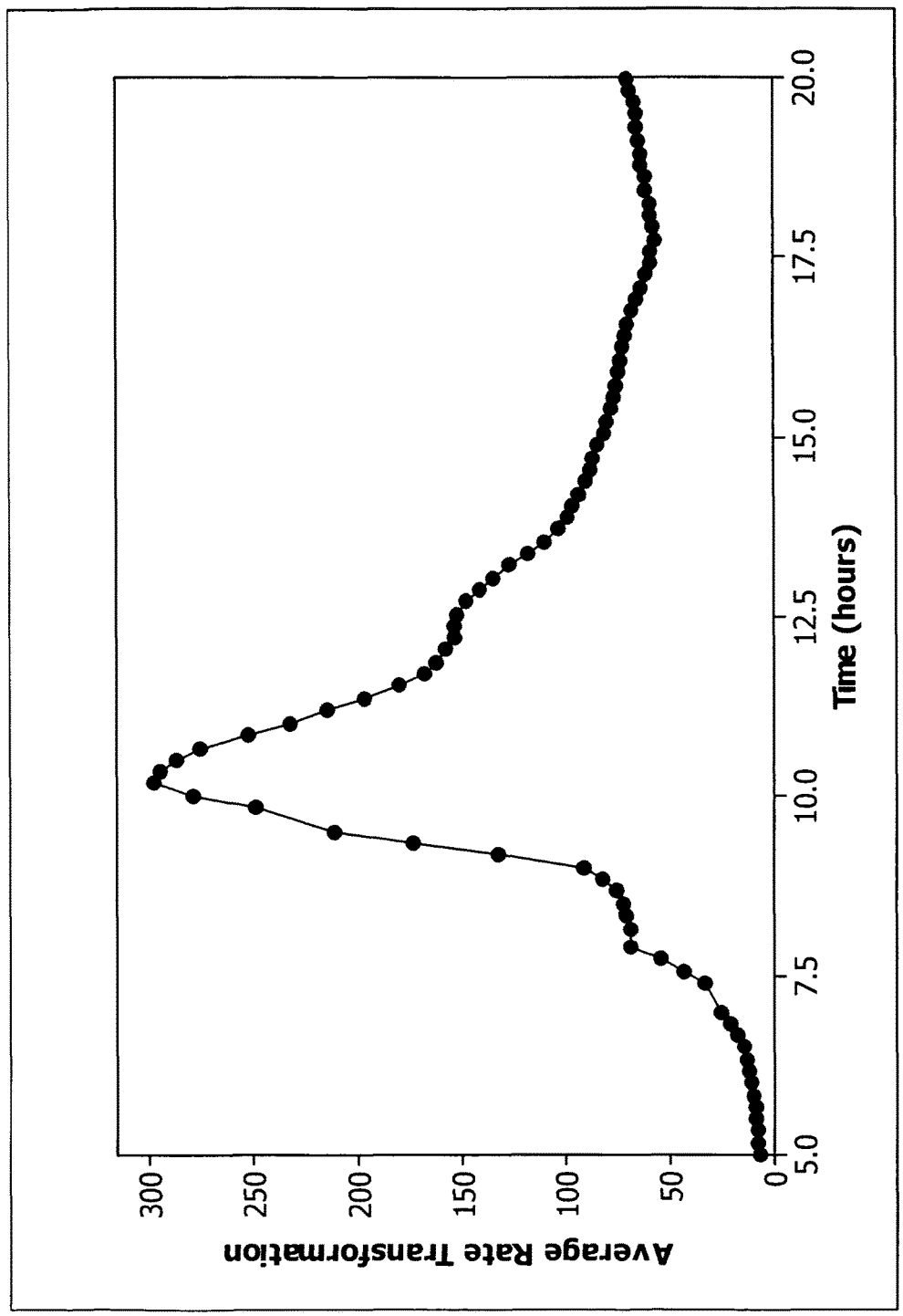
FIG. 9 is a plot of average rate transformation versus time for a clinical *Enterococcus faecalis* false negative.

The BACTEC® system applies a series of algorithms to the signal data that can trigger the system to identify a vessel with a positive status based on the occurrence of a "knee" or the presence of a change in rate or acceleration in the sequence of data. There is no attempt to qualify this determination to add a confidence to this status change. Confidence can be added to the prior art detection algorithm by counting the number of times a set of algorithms are triggered for a vessel in protocol. The more times an algorithm was triggered to indicate a positive status then the more confidence in the change in status to positive. Although this would certainly increase confidence in the result for many cultures it is based on an indicator method that is limited in its ability to adequately and robustly provide the confidence desired in any determination in a diagnostic system. As an example, in the external clinical evaluation of the modified Aerobic plus medium a false negative culture was observed when using conventional microorganism detection algorithms rather than the algorithms disclosed in the present invention. The culture was found to contain *Enterococcus faecalis* when subcultured at the end of protocol. The data was inspected and it was determined that two door opening events (at 7.0 and 7.9 hours into protocol), where the door to the BACTEC® system was literally opened (with concomitant temperature transient events that affected the temperature), compensated signal data and caused the prior art detection algorithms to fail. Applying the ART transformation to the data would have allowed robust detection (possibly delayed by as much as 2 hours). In addition, by applying a threshold based on the ART data (conservatively and an ART value of 100 or greater as positive) this vessel would be detected by the system on every subsequent reading for up to fourteen hours in protocol (instrument positive on every test cycle for as long as 5 hours). The use of both the ART and the NR transformation (with positive threshold) could have extended the period of positive detection possibly to the end of protocol. The point being that the use of these transformation provides a very high degree of confidence that a vessel is positive, even vessels that have detected as false negative on the current system. FIGS. 7, 8 and 9 show data for a culture that was found to contain *Enterococcus faecalis* when subcultured at the end of protocol. The data in these figures establish that the inventive methods disclosed herein also detect this microorganism infection. FIG. 7 is a plot of compensated fluorescent signal versus time for a clinical *Enterococcus faecalis* false negative. FIG. 8 is a plot of normalized relative values versus time for a clinical *Enterococcus faecalis* false negative. FIG. 9 is a plot of average rate transformation versus time for a clinical *Enterococcus faecalis* false negative. Using the methods of the present invention, the culture would have been found to contain microorganisms.

7 REFERENCES CITED

All references cited herein are incorporated herein by reference in their entirety and for all purposes to the same extent as if each individual publication or patent or patent application was specifically and individually indicated to be incorporated by reference in its entirety herein for all purposes.

8 MODIFICATIONS

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:
1. A method comprising:
   (A) incubating, with an incubator, a culture disposed within a vessel during portions of a time interval between a first time point and a second time point, wherein the culture comprises a sample and a culture media;
   (B) measuring, with a sensor, a biological state of the culture at a plurality of time points between the first time point and the second time point, wherein the biological state is one of $CO_2$ concentration, $O_2$ concentration, pH, a rate of change in $CO_2$ concentration, a rate of change in $O_2$ concentration, or a rate of change in pH;
   (C) determining, with one or more processors, a plurality of rate transformation values, wherein each rate transformation value is derived from a different subset of the measurements of the biological state of the culture within a predetermined time interval;
   (D) determining, with the one or more processors, a plurality of average relative transformation values, wherein each average relative transformation value is derived from a different subset of the rate transformation values;
   (E) determining, with the one or more processors, that the culture contains a plurality of microorganisms when (i) at least one average relative transformation value exceeds a first threshold value or (ii) an extent of growth exhibited by the culture exceeds a second threshold value, wherein the extent of growth is derived from one or more of the measurements of the biological state of the culture; and
   (F) processing the vessel to confirm the presence of the plurality of microorganisms after it is determined in step (E) that the culture contains a plurality of microorganisms.

2. The method of claim 1, wherein processing the vessel to confirm the presence of the plurality of microorganisms in step (F) comprises at least one of (i) preparing a gram stain or (ii) preparing a subculture on a plated medium.

3. The method of claim 1 further comprising:
   initiating processes for microorganism identification and antimicrobial susceptibility testing when it is confirmed in step (F) that the culture contains a plurality of microorganisms.

4. The method of claim 1 further comprising:
   displaying the determination of step (E) on a user interface device.

5. The method of claim 1, wherein the sensor used in step (B) to measure the biological state of the culture at the plurality of time points is a fluorescent $CO_2$ sensor.

6. The method of claim 1, wherein each rate transformation value is a first derivative of a different subset of the measurements of the biological state of the culture within a predetermined time interval.

7. The method of claim 1, wherein the determination of step (E) is made when the at least one average relative transformation value exceeds the first threshold value.

8. The method of claim 1 further comprising:
   converting the measurements of the biological state of the culture into normalization relative values.

9. The method of claim 8, wherein each rate transformation value is a first derivative of a different subset of the normalization relative values within a predetermined time interval.

10. The method of claim 9, wherein the determination of step (E) is made when the extent of growth exhibited by the culture exceeds the second threshold value.

11. The method of claim 10, wherein the extent of growth (EG) is determined by the equation:

$$EG = NR_{after\_growth} - NR_{minimum\_growth},$$

wherein:
   $NR_{after\_growth}$ is a normalization relative value in the plurality of normalization relative values that was used in the calculation of (i) a maximum average relative transformation value in the plurality of average relative transformation values, (ii) a first average relative transformation value following the maximum average relative transformation value, or (iii) a first average relative transformation value preceding the maximum average relative transformation value; and
   $NR_{minimum\_growth}$ is a normalization relative value in the plurality of normalization relative values that was used in the calculation of a first average relative transformation value to achieve a third threshold value.

12. The method of claim 1, wherein the determination of step (E) is made when (i) the at least one average relative transformation value exceeds the first threshold value and (ii) the extent of growth exhibited by the culture exceeds the second threshold value.

13. The method of claim 1, wherein all of the predetermined time intervals have the same duration.

14. The method of claim 13, wherein the rate transformation values are calculated and stored in successive instances.

15. The method of claim 14, wherein the average relative transformation values are calculated and stored in successive instances.

16. An apparatus comprising:
   (A) one or more processors;
   (B) an incubator for incubating a culture disposed within a vessel during portions of a time interval between a first time point and a second time point, wherein the culture comprises a sample and a culture media;
   (C) a sensor for measuring a biological state of the culture at a plurality of time points between the first time point and the second time point, wherein the biological state is one of $CO_2$ concentration, $O_2$ concentration, pH, a rate of change in $CO_2$ concentration, a rate of change in $O_2$ concentration, or a rate of change in pH; and (D) a memory comprising:
  (1) a first threshold value;
  (2) a second threshold value; and
  (3) a culture determination module comprising:
    (a) electronically encoded instructions for determining a plurality of rate transformation values, wherein each rate transformation value is derived from a different subset of the measurements of the biological state of the culture within a predetermined time interval;
    (b) electronically encoded instructions for determining a plurality of average relative transformation values, wherein each average relative transformation value is derived from a different subset of the rate transformation values; and
    (c) electronically encoded instructions for determining that the culture contains a plurality of microorganisms when (i) at least one average relative transformation value exceeds the first threshold value or (ii) an extent of growth exhibited by the culture exceeds the second threshold value, wherein the extent of growth is derived from one or more of the measurements of the biological state of the culture; and
(E) a user interface configured to notify a user that the vessel should be processed to confirm the presence of the plurality of microorganisms after it is determined that the culture contains a plurality of microorganisms.

17. The apparatus of claim 16, wherein the user interface is configured to display the notification on a monitor.

18. The apparatus of claim 16, wherein the electronically encoded instructions (iii) determine that the culture contains a plurality of microorganisms when (i) the at least one average relative transformation value exceeds the first threshold value and (ii) the extent of growth exhibited by the culture exceeds the second threshold value.

19. The apparatus of claim 16, wherein the culture determination module further comprises electronically encoded instructions for converting the measurements of the biological state of the culture into normalization relative values.

20. The apparatus of claim 19, wherein each rate transformation value is a first derivative of a different subset of the normalization relative values within a predetermined time interval.

* * * * *